US008540991B2

(12) United States Patent
Alper

(10) Patent No.: US 8,540,991 B2
(45) Date of Patent: Sep. 24, 2013

(54) MONOCLONAL ANTIBODIES AGAINST PCBP-1 ANTIGENS, AND USES THEREFOR

(75) Inventor: Özge Alper, Bethesda, MD (US)

(73) Assignee: Alper Biotech, LLC, Rockville, MD (US)

( * ) Notice: Subject to any disclaimer, the term of this patent is extended or adjusted under 35 U.S.C. 154(b) by 0 days.

(21) Appl. No.: 13/568,969

(22) Filed: Aug. 7, 2012

(65) Prior Publication Data

US 2012/0301395 A1 Nov. 29, 2012

Related U.S. Application Data

(63) Continuation of application No. 12/684,090, filed on Jan. 7, 2010, now abandoned.

(60) Provisional application No. 61/172,457, filed on Apr. 24, 2009.

(51) Int. Cl.
*A61K 39/395* (2006.01)
(52) U.S. Cl.
USPC .................. 424/138.1; 424/139.1; 424/141.1; 424/142.1
(58) Field of Classification Search
None
See application file for complete search history.

(56) References Cited

U.S. PATENT DOCUMENTS

2004/0137513 A1 7/2004 Devaux et al.
2006/0121022 A1 6/2006 Koga et al.

FOREIGN PATENT DOCUMENTS

| EP | 1 775 590 A1 | 4/2007 |
| JP | 2008-164517 | 7/2008 |
| WO | WO 2009/068254 A1 | 6/2009 |
| WO | WO 2012/009577 A2 | 1/2012 |

OTHER PUBLICATIONS

Acs et al., "Differential Expression of E-Cadherin in Lobular and Ductal Neoplasms of the Breast and its Biologic and Diagnostic Implications," *Am. J. Clin. Pathol.* 115:85-98 (2001).
Bedolla et al., "Nuclear Versus Cytoplasmic Localization of Filamin A in Prostate Cancer: Immunohistochemical Correlation with Metastases," Clin. Cancer Res. 15(3):788-786 (2009).
Chkheidze et al., "A Novel Set of Nuclear Localization Signals Determine Distributions of the αCP RNA-Binding Proteins," *Mol. Cell. Biol.* 23(23):8405-8415 (2003).
Dobbyn et al., "Regulation of BAG-1 IRES-Mediated Translation Following Chemotoxic Stress," *Oncogene* 27:1167-1174 (2008).
Giretti et al., "Extra-Nuclear Signalling of Estrogen Receptor to Breast Cancer Cytoskeletal Remodelling, Migration and Invasion," *PLos One* 3(5):E2238 (2008).
International Preliminary Report on Patentability mailed Jan. 15, 2013 in PCT/US2011/044080.
International Search Report mailed Jul. 14, 2010 in application No. PCT/US2011/044080.

O'Malley et al., "Nuclear Receptor Coregulators in Cancer Biology," *Cancer Res.* 69(21):8217-8222 (2009).
Pestalozzi, B.C., "Brain Metastases and Subtypes of Breast Cancer," *Ann. Oncol.* 20(5):803-805 (2009).
Thakur et al., "Regulation of BRCA1 Transcription by Specific Single-Stranded DNA Binding Factors," *Mol. Cell. Biol.* 23(11):3774-3787 (2003).
Wang et al., "PCBP1 Suppresses the Translation of Metastasis-Associated PRL-3 Phosphatase," *Cancer Cell* 18:52-62 (2010).
Written Opinion of the International Searching Authority mailed Mar. 21, 2012 in PCT/US2011/044080.
Zhang, et al., "PCBP-1 Regulates Alternative Splicing of the CD44 Gene and Inhibits Invasion in Human Hepatoma Cell Line HepG2 Cells," *Mol. Cancer* 9(72):1-10 (2010).
Casset et al., "A peptide mimetic of an anti-CD4 monoclonal antibody by rational design," *Biochemical and Biophysical Research Communications* 307:198-205 (2003).
Gamarnik et al., "Two functional complexes formed by KH domain containing proteins with the 5' noncoding region of poliovirus RNA," *RNA* 3:882-892 (1997).
Gromov et al., "Up-regulated Proteins in the Fluid Bathing the Tumour Cell Microenvironment as Potential Serological Markers for Early Detection of Cancer of the Breast", *Molecular Oncology* 4:65-89 (2010).
Holm et al., "Functional mapping and single chain construction of the anti-cytokeratin 8 monoclonal antibody TS1," *Molecular Immunology* 44:1075-1084 (2007).
International Search Report mailed Mar. 30, 2010 in application No. PCT/US2010/020401.
Mac Callum et al., "Antibody-antigen interactions: contact analysis and binding site topography," *Journal of Molecular Biology* 262:732-745 (1996).
Pillai et al., "Expression of folate receptors and heterogeneous nuclear ribonucleoprotein E1 in women with human papillomavirus mediated transformation of cervical tissue to cancer," *J Clin Pathol* 56:569-574 (2003).

(Continued)

*Primary Examiner* — Sean E Aeder
*Assistant Examiner* — Julie Wu
(74) *Attorney, Agent, or Firm* — Finnegan, Henderson, Farabow, Garrett & Dunner, LLP

(57) ABSTRACT

The present invention provides and includes monoclonal antibodies (MoAbs or mAbs) specific or preferentially selective for PCBP-1 antigens, hybridoma lines that secrete these PCBP-1 antibodies or antibody fragments, and the use of such antibodies and antibody fragments to detect PCBP-1 antigens, particularly those expressed by cancer cells. The present invention also includes antibodies that are specific for or show preferential binding to a soluble form of PCBP-1. The present invention further includes chimeric and humanized antibodies, processes for producing monoclonal, chimeric, and humanized antibodies using recombinant DNA technology, and their therapeutic uses, particularly in the treatment of cancer. The present invention further includes methods and kits for the immunodetection and immunotherapy of cells for samples which express PCBP-1 antigens.

15 Claims, 28 Drawing Sheets

(56) References Cited

OTHER PUBLICATIONS

Rudikoff et al., "Single amino acid substitution altering antigen-binding specificity," *Proceedings of the National Academy of Sciences* 79:1979-1983 (1982).

Vajdos et al., "Comprehensive functional maps of the antigen binding site of an ant ErbB2 antibody obtained with shotgun scanning mutagenesis," *Journal of Molecular Biology* 320:415-428 (2002).

Wu et al., "Humanization of a murine monoclonal antibody by simultaneous optimization of framework and CDR residues," *Journal of Molecular Biology* 294:151-162 (1999).

Alper BioTech, "Alper Biotech PCBP-1 IHC Kit: for immunohistochemical staining of PCBP1 (Poly(rC))-binding protein 1 in FFPE Tissue," released Apr. 17, 2010 in Alper BioTech Kit, Catalog No. AB1, 4 pages.

Balint et al., "Antibody engineering by parsimonious mutagenesis," *Gene* 137:109-118 (1993).

Casset et ai., "A peptide mimetic of an anti-CD4 monoclonal antibody by rational design," *Biochemical and Biophysical Research Communications* 307:198-205 (2003).

Chen et al., "Selection and analysis of an optimized anti-VEGF antibody: crystal structure of an affinity matured Fab in complex with antigen," *Journal of Molecular Biology* 293:865-881 (1999).

Database WPI Week 200851, XP 002572783 (2008).

De Pascalis et al., "Grafting of abbreviated complementarity determining regions containing specificity determining residues essential for ligand contact to engineer a less immunogenic humanized monoclonal antibody," *Journal of Immunology* 169:3076-3084 (2002).

Gamarnik et al., "Two functional complexes formed by KH domain containing proteins with the 5' noncoding region of poliovirus RNA," *RNA* 3:882-892 (1997).

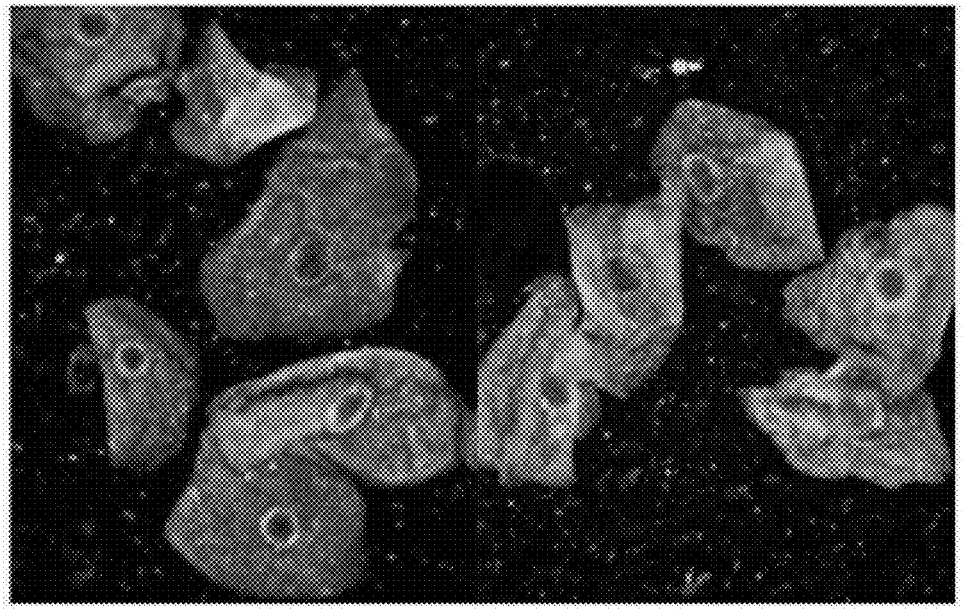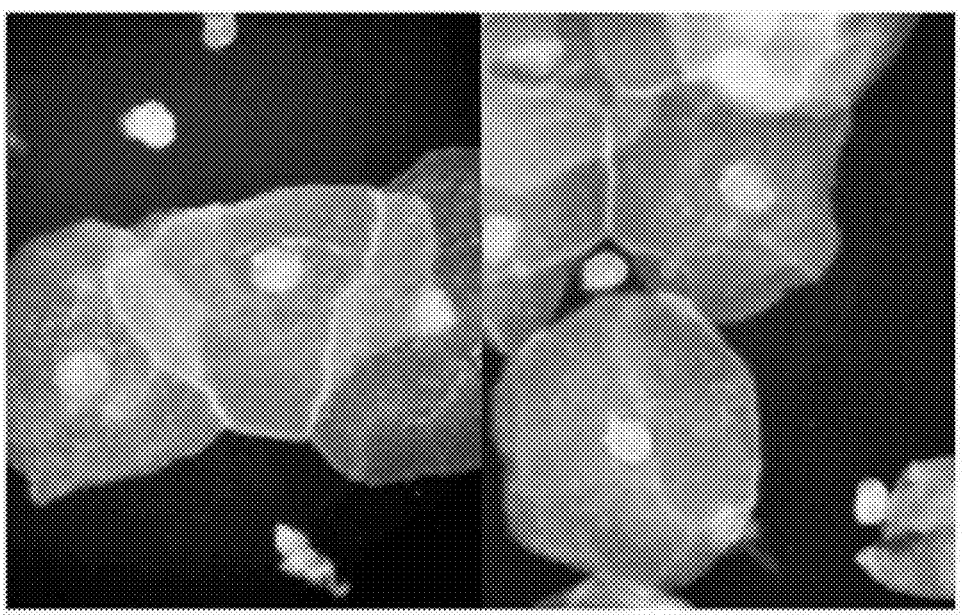
FIG. 4

| M | | NM | | C | |
|---|---|---|---|---|---|
| 212 | 196 | 436 | 518 | 324 | 286 |
| 299 | 247 | 628 | 796 | 410 | 365 |
| 259 | 358 | 632 | 653 | 590 | 483 |
| 301 | 342 | 534 | 598 | 459 | 531 |
| 349 | 333 | 413 | 534 | 432 | 541 |
| 322 | 293 | 514 | 571 | 416 | 520 |
| 336 | 350 | 435 | 456 | 452 | 518 |
| 285 | 306 | 460 | 464 | 474 | 511 |
| 268 | 323 | 493 | 553 | 510 | 546 |
| 246 | 307 | 483 | 491 | 527 | 540 |
| 329 | 317 | 484 | 489 | 371 | 325 |
| 281 | 338 | 577 | 516 | 611 | 517 |
| 290.5833 | 309.1667 | 507.4167 | 553.25 | 464.6667 | 473.5833 |
| 299.875 | | 530.3333 | | 469.125 | |
| M | M | NM | NM | C | C |
| 291.9323 | 321.4524 | 496.2188 | 503.1786 | 487.0952 | 487.4635 |

*FIG. 9*

1:10 DILUTED THEN 20ul IS TAKEN FROM 1:10 DILUTION AND ADDED ON TO 90ul PBS

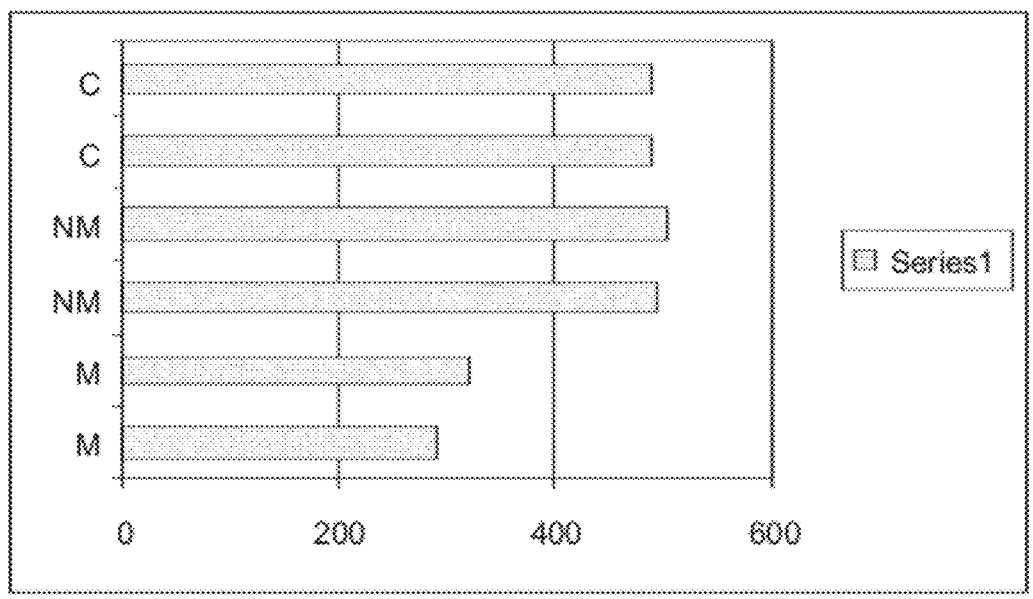
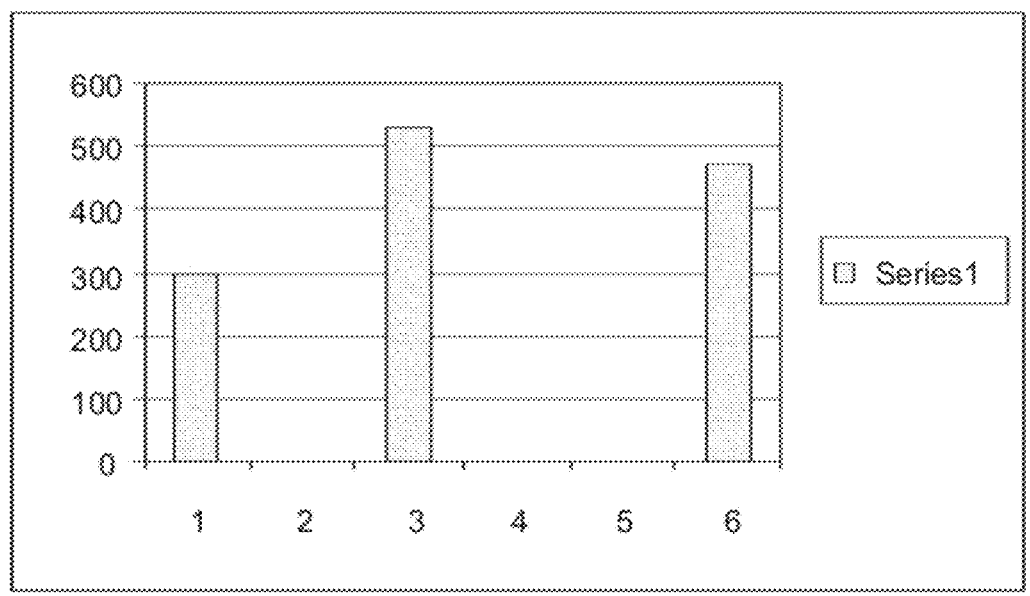
FIG. 9 (CONT)

BLASTN 2.2.17 [AUG-26-2007]

DATABASE: MGALLNCSEQ  630 SEQUENCES; 184,796 TOTAL LETTERS

QUERY= TMPSEQ_0  (1324 LETTERS)

| SEQUENCES PRODUCING SIGNIFICANT ALIGNMENTS: | SCORE (BITS) | E VALUE |
|---|---|---|
| J558.18 | 433 | e-123 |
| VMU-3.2 | 411 | e-116 |
| J558.85.191 | 411 | e-116 |
| J558.83.189 | 402 | e-113 |
| J558.29 | 361 | e-101 |
| J558.27 | 353 | 6e-99 |
| J558.87.193 | 350 | 5e-98 |
| VHA1 | 349 | 2e-97 |
| J558.30 | 349 | 2e-97 |
| J558.18A | 347 | 4e-97 |

DOMAIN CLASSIFICATION REQUESTED: KABAT SYSTEM

BLASTN 2.2.17 [Aug-26-2007]

Database: mgalincseq 630 sequences; 184,796 total letters

Query: tmpseq_0 (1055 letters)

SEQUENCES PRODUCING SIGNIFICANT ALIGNMENTS:

| | Score (bits) | E Value |
|---|---|---|
| 21-12 | 428 | e-121 |
| 21-7 | 394 | e-111 |
| 21-4 | 338 | 7e-94 |
| 21-10 | 333 | 6e-93 |
| 21-8 | 329 | 2e-91 |
| 21-3 | 327 | 4e-91 |
| 21-5 | 324 | 4e-90 |
| 21-2 | 319 | 1e-88 |
| 21-9 | 307 | 6e-85 |
| 21-1 | 307 | 6e-85 |
| 21-12 | 428 | e-121 |

DOMAIN CLASSIFICATION: KABAT SYSTEM

| SEQ ID NO. | MEASURED MASS, AMU (AVERAGE) | CALCULATED MASS, AMU (AVERAGE) | ERROR AMU | SEQUENCE POSITION START | SEQUENCE POSITION END | SEQUENCE |
|---|---|---|---|---|---|---|
| 1 | 917.06 | 916.98 | 0.08 | 39 | 46 | IREESGAR |
| 2 | 1302.39 | 1302.41 | -0.02 | 47 | 57 | INISEGNCPER Propionamide (C) |
| 3 | 1388.69 | 1388.65 | 0.04 | 58 | 70 | IITLTGPTN4FK |
| 4 | 3379.88 | 3379.82 | 0.07 | 71 | 101 | AFAMIDKLEEDINSSMTNSTAASRPPVTLR |
| 4 | 3395.03 | 3395.81 | 0.22 | 71 | 101 | AFAMIDKLEEDINSSMTNSTAASRPPVTLR Oxidation (M) |
| 5 | 1456.86 | 1456.75 | 0.11 | 102 | 115 | LVVPATOCGSLIGK Propionamide (C) |
| 6 | 2090.24 | 2090.23 | 0.01 | 125 | 144 | ESTGAOVOVAGDMLPNSTER |
| 6 | 2106.35 | 2106.23 | 0.12 | 125 | 144 | ESTGAOVOVAGDMLPNSTER Oxidation (M) |
| 7 | 1687.18 | 1686.97 | 0.22 | 145 | 160 | AITIAGVPOSVTECVK Propionamide (C) |
| 8 | 1974.30 | 1974.31 | 0.12 | 161 | 177 | QICLVLMETLSQSPQGR Propionamide (C) |
| 8 | 1990.42 | 1990.31 | 0.12 | 161 | 177 | QICLVLMETLSQSPQGR Oxidation (M); Propionamide (C) |
| 9 | 2489.80 | 2489.89 | -0.09 | 178 | 200 | VMTIPYOPMPASSPVICAGGODR Propionamide (C) |
| 9 | 2505.93 | 2505.89 | 0.05 | 178 | 200 | VMTIPYOPMPASSPVICAGGODR Oxidation (M); Propionamide (C) |
| 9 | 2522.04 | 2521.89 | 0.16 | 178 | 200 | VMTIPYOPMPASSPVICAGGODR 2 Oxidation (M); Propionamide (C) |
| 10 | 2608.86 | 2608.84 | 0.02 | 244 | 268 | QQSHFAMMHGGTGFAGIDSSSPEVK |
| 10 | 2622.79 | 2622.84 | -0.05 | 244 | 268 | QQSHFAMMHGGTGFAGIDSSSPEVK Oxidation (M) |
| 10 | 2638.91 | 2638.84 | 0.07 | 244 | 268 | QQSHFAMMHGGTGFAGIDSSSPEVK 2 Oxidation (M) |
| 11 | 3216.38 | 3216.58 | -0.20 | 269 | 297 | GYHASLDASTQTTHELTIPNNILGOIGR Propionamide (C) |
| 12 | 1086.29 | 1086.16 | 0.14 | 315 | 325 | IANPVEGSSGR |
| 13 | 2177.46 | 2177.46 | 0.01 | 326 | 346 | QVTITGSAASISLAOYLINAR |
| 14 | 1014.19 | 1014.13 | 0.06 | 347 | 356 | LSSEKGMGCS Oxidation (M) |

FIG. 12

PCBP-1 EXPRESSION IN HUMAN NORMAL AND CANCER TISSUES

| TISSUE | INTENSITY | TISSUE | INTENSITY |
|---|---|---|---|
| NORMAL COLON | + | COLON CANCER | ++ |
| NORMAL SKIN | + | MELANOMA | ++ |
| NORMAL SKIN | + | SQUAMOUS CARCINOMA | ++/+++ |
| NORMAL BRAIN | - | GLIOBLASTOMA MULTIFORME | + |
| NORMAL OVARY | +++ | OVARIAN CANCER | +/- |
| NORMAL ENDOMETRIUM | +/- | ENDOMETRIAL CANCER | +++ |
| NORMAL MUSCLE | + | SARCOMA | ++ |
| NORMAL BLADDER | + | BLADDER CANCER | ++ |

SEQUENCE LISTING

```
<160> NUMBER OF SEQ ID NOS: 50

<210> SEQ ID NO 1
<211> LENGTH: 8
<212> TYPE: PRT
<213> ORGANISM: Homo sapiens

<400> SEQUENCE: 1

Ile Arg Glu Glu Ser Gly Ala Arg
1               5

<210> SEQ ID NO 2
<211> LENGTH: 11
<212> TYPE: PRT
<213> ORGANISM: Homo sapiens

<400> SEQUENCE: 2

Ile Asn Ile Ser Glu Gly Asn Cys Pro Glu Arg
1               5                   10

<210> SEQ ID NO 3
<211> LENGTH: 13
<212> TYPE: PRT
<213> ORGANISM: Homo sapiens

<400> SEQUENCE: 3

Ile Ile Thr Leu Thr Gly Pro Thr Asn Ala Ile Phe Lys
1               5                   10

<210> SEQ ID NO 4
<211> LENGTH: 31
<212> TYPE: PRT
<213> ORGANISM: Homo sapiens

<400> SEQUENCE: 4

Ala Phe Ala Met Ile Ile Asp Lys Leu Glu Glu Asp Ile Asn Ser Ser
1               5                   10                  15

Met Thr Asn Ser Thr Ala Ala Ser Arg Pro Pro Val Thr Leu Arg
            20                  25                  30
```

```
<210> SEQ ID NO 5
<211> LENGTH: 14
<212> TYPE: PRT
<213> ORGANISM: Homo sapiens

<400> SEQUENCE: 5

Leu Val Val Pro Ala Thr Gln Cys Gly Ser Leu Ile Gly Lys
1               5                   10

<210> SEQ ID NO 6
<211> LENGTH: 20
<212> TYPE: PRT
<213> ORGANISM: Homo sapiens

<400> SEQUENCE: 6

Glu Ser Thr Gly Ala Gln Val Gln Val Ala Gly Asp Met Leu Pro Asn
1               5                   10                  15

Ser Thr Glu Arg
            20

<210> SEQ ID NO 7
<211> LENGTH: 16
<212> TYPE: PRT
<213> ORGANISM: Homo sapiens

<400> SEQUENCE: 7

Ala Ile Thr Ile Ala Gly Val Pro Gln Ser Val Thr Glu Cys Val Lys
1               5                   10                  15

<210> SEQ ID NO 8
<211> LENGTH: 17
<212> TYPE: PRT
<213> ORGANISM: Homo sapiens

<400> SEQUENCE: 8

Gln Ile Cys Leu Val Met Leu Glu Thr Leu Ser Gln Ser Pro Gln Gly
1               5                   10                  15

Arg

<210> SEQ ID NO 9
<211> LENGTH: 23
<212> TYPE: PRT
<213> ORGANISM: Homo sapiens

<400> SEQUENCE: 9

Val Met Thr Ile Pro Tyr Gln Pro Met Pro Ala Ser Ser Pro Val Ile
1               5                   10                  15

Cys Ala Gly Gly Gln Asp Arg
            20

<210> SEQ ID NO 10
<211> LENGTH: 25
<212> TYPE: PRT
<213> ORGANISM: Homo sapiens

<400> SEQUENCE: 10

Gln Gln Ser His Phe Ala Met Met His Gly Gly Thr Gly Phe Ala Gly
1               5                   10                  15

Ile Asp Ser Ser Ser Pro Glu Val Lys
            20                  25
```

```
<210> SEQ ID NO 11
<211> LENGTH: 29
<212> TYPE: PRT
<213> ORGANISM: Homo sapiens

<400> SEQUENCE: 11

Gly Tyr Trp Ala Ser Leu Asp Ala Ser Thr Gln Thr Thr His Glu Leu
1               5                   10                  15

Thr Ile Pro Asn Asn Leu Ile Gly Cys Ile Ile Gly Arg
            20                  25

<210> SEQ ID NO 12
<211> LENGTH: 11
<212> TYPE: PRT
<213> ORGANISM: Homo sapiens

<400> SEQUENCE: 12

Ile Ala Asn Pro Val Glu Gly Ser Ser Gly Arg
1               5                   10

<210> SEQ ID NO 13
<211> LENGTH: 21
<212> TYPE: PRT
<213> ORGANISM: Homo sapiens

<400> SEQUENCE: 13

Gln Val Thr Ile Thr Gly Ser Ala Ala Ser Ile Ser Leu Ala Gln Tyr
1               5                   10                  15

Leu Ile Asn Ala Arg
            20

<210> SEQ ID NO 14
<211> LENGTH: 10
<212> TYPE: PRT
<213> ORGANISM: Homo sapiens

<400> SEQUENCE: 14

Leu Ser Ser Glu Lys Gly Met Gly Cys Ser
1               5                   10

<210> SEQ ID NO 15
<211> LENGTH: 345
<212> TYPE: DNA
<213> ORGANISM: Mus sp.
<220> FEATURE:
<221> NAME/KEY: CDS
<222> LOCATION: (1)..(345)

<400> SEQUENCE: 15 gtg cag ctg gag gag tct gga cct gag ctg gtg aag cct ggg gcc tca        48
Val Gln Leu Glu Glu Ser Gly Pro Glu Leu Val Lys Pro Gly Ala Ser
1               5                   10                  15 gtg aag att tcc tgc aaa gtt tct ggc tac gca ttc agt agg tct tgg        96
Val Lys Ile Ser Cys Lys Val Ser Gly Tyr Ala Phe Ser Arg Ser Trp
            20                  25                  30 atg aac tgg gtg aag cag agg cct gga cag ggt ctt gag tgg att gga       144
Met Asn Trp Val Lys Gln Arg Pro Gly Gln Gly Leu Glu Trp Ile Gly
        35                  40                  45 cgg atc tat cct gga gat gga gat act aac tac aat ggg aag ttc aag       192
Arg Ile Tyr Pro Gly Asp Gly Asp Thr Asn Tyr Asn Gly Lys Phe Lys
    50                  55                  60 ggc aag gcc aca ctg act gca gac aaa tcc tcc agt aca gcc tac atg       240
Gly Lys Ala Thr Leu Thr Ala Asp Lys Ser Ser Ser Thr Ala Tyr Met
65                  70                  75                  80
```

```
cag ctc agc agc ctg acc tct gtg gac tct gcg gtc tat ttc tgt gca    288
Gln Leu Ser Ser Leu Thr Ser Val Asp Ser Ala Val Tyr Phe Cys Ala
                85                  90                  95 aga tcg gaa cta tgg tca aaa atg ttt gct tac tgg ggc caa ggg acc    336
Arg Ser Glu Leu Trp Ser Lys Met Phe Ala Tyr Trp Gly Gln Gly Thr
            100                 105                 110 acg gtc aca                                                        345
Thr Val Thr
        115

<210> SEQ ID NO 16
<211> LENGTH: 115
<212> TYPE: PRT
<213> ORGANISM: Mus sp.

<400> SEQUENCE: 16

Val Gln Leu Glu Glu Ser Gly Pro Glu Leu Val Lys Pro Gly Ala Ser
1               5                   10                  15

Val Lys Ile Ser Cys Lys Val Ser Gly Tyr Ala Phe Ser Arg Ser Trp
            20                  25                  30

Met Asn Trp Val Lys Gln Arg Pro Gly Gln Gly Leu Glu Trp Ile Gly
        35                  40                  45

Arg Ile Tyr Pro Gly Asp Gly Asp Thr Asn Tyr Asn Gly Lys Phe Lys
    50                  55                  60

Gly Lys Ala Thr Leu Thr Ala Asp Lys Ser Ser Ser Thr Ala Tyr Met
65                  70                  75                  80

Gln Leu Ser Ser Leu Thr Ser Val Asp Ser Ala Val Tyr Phe Cys Ala
                85                  90                  95

Arg Ser Glu Leu Trp Ser Lys Met Phe Ala Tyr Trp Gly Gln Gly Thr
            100                 105                 110

Thr Val Thr
        115

<210> SEQ ID NO 17
<211> LENGTH: 294
<212> TYPE: DNA
<213> ORGANISM: Mus sp.
<220> FEATURE:
<221> NAME/KEY: CDS
<222> LOCATION: (1)..(294)

<400> SEQUENCE: 17 cag gtc cag ctg cag cag tct gga cct gag ctg gtg aag cct ggg gcc    48
Gln Val Gln Leu Gln Gln Ser Gly Pro Glu Leu Val Lys Pro Gly Ala
1               5                   10                  15 tca gtg aag att tcc tgc aaa gct tct ggc tac gca ttc agt agc tct    96
Ser Val Lys Ile Ser Cys Lys Ala Ser Gly Tyr Ala Phe Ser Ser Ser
            20                  25                  30 tgg atg aac tgg gtg aag cag agg cct gga cag ggt ctt gag tgg att    144
Trp Met Asn Trp Val Lys Gln Arg Pro Gly Gln Gly Leu Glu Trp Ile
        35                  40                  45 gga cgg att tat cct gga gat gga gat act aac tac aat ggg aag ttc    192
Gly Arg Ile Tyr Pro Gly Asp Gly Asp Thr Asn Tyr Asn Gly Lys Phe
    50                  55                  60 aag ggc aag gcc aca ctg act gca gac aaa tcc tcc agc aca gcc tac    240
Lys Gly Lys Ala Thr Leu Thr Ala Asp Lys Ser Ser Ser Thr Ala Tyr
65                  70                  75                  80
```

```
atg cag ctc agc agc ctg acc tct gtg gac tct gcg gtc tat ttc tgt    288
Met Gln Leu Ser Ser Leu Thr Ser Val Asp Ser Ala Val Tyr Phe Cys
                85                  90                  95 gca aga                                                            294
Ala Arg

<210> SEQ ID NO 18
<211> LENGTH: 98
<212> TYPE: PRT
<213> ORGANISM: Mus sp.

<400> SEQUENCE: 18

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Met Asn Trp Val Lys Gln Arg Pro Gly Gln Gly Leu Glu Trp Ile
        35                  40                  45

Gly Arg Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Val Asp Ser Ala Val Tyr Phe Cys
                85                  90                  95

Ala Arg

<210> SEQ ID NO 19
<211> LENGTH: 291
<212> TYPE: DNA
<213> ORGANISM: Mus sp.

<400> SEQUENCE: 19
gttcagctgc agcagtctgg acctgagctg gtgaagcctg gggcctcagt gaagatttcc     60
tgcaaggctt ctggctacgc attcagtagc tcctggatga actgggtgaa gcagaggcct    120
ggaaagggtc ttgagtggat tgacggatt tatcctggag atggagatac taactacaat    180
gggaagttca aggcaaggc cacactgact gcagacaaat cctccagcac agcctacatg    240
caactcagca gcctgacatc tgaggactct gcggtctact tctgtgcaag a            291

<210> SEQ ID NO 20
<211> LENGTH: 291
<212> TYPE: DNA
<213> ORGANISM: Mus sp.

<400> SEQUENCE: 20
gttcagctgc agcagtctgg acctgagctg gtgaagcctg gggcctcagt gaagatttcc     60
tgcaaggctt ctggctacgc attcagtagc tcctggatga actgggtgaa gcagaggcct    120
ggaaagggtc ttgagtggat tgacggatt tatcctggag atggagatac taactacaat    180
gggaagttca aggcaaggc cacactgact gcagacaaat cctccagcac agcctacatg    240
caactcagca gcctgacatc tgaggactct gcggtctact tctgtgcaag a            291

<210> SEQ ID NO 21
<211> LENGTH: 33
<212> TYPE: DNA
<213> ORGANISM: Mus sp.

<400> SEQUENCE: 21
gtttgcttac tggggccaag ggactctggt cac                                  33
```

```
<210> SEQ ID NO 22
<211> LENGTH: 33
<212> TYPE: DNA
<213> ORGANISM: Mus sp.

<400> SEQUENCE: 22
tttgactact ggggccaagg caccactctc aca                              33

<210> SEQ ID NO 23
<211> LENGTH: 291
<212> TYPE: DNA
<213> ORGANISM: Mus sp.

<400> SEQUENCE: 23
gttcagctgc agcagtctgg ggctgagctg gtgaagcctg gggcctcagt gaagatttcc    60
tgcaaagctt ctggctacgc attcagtagc tactggatga actgggtgaa gcagaggcct   120
ggaaagggtc ttgagtggat tggacagatt tatcctggag atggtgatac taactacaac   180
ggaaagttca aggcaaggc cacactgact gcagacaaat cctccagcac agcctacatg   240
cagctcagca gcctgacctc tgaggactct gcggtctatt tctgtgcaag a            291

<210> SEQ ID NO 24
<211> LENGTH: 291
<212> TYPE: DNA
<213> ORGANISM: Mus sp.

<400> SEQUENCE: 24
gtccagctgc agcagtctgg acctgagctg gtgaagcctg ggcttcagt gaggatatcc    60 tgcaaggctt ctggctacac cttcacaagc tactatatac actgggtgaa gcagaggcct   120
ggacagggac ttgagtggat tggatggatt tatcctggaa atgttaatac taagtacaat   180
gagaagttca aggcaaggc cacactgact gcagacaaat cctccagcac agcctacatg   240
cagctcagca gcctgacctc tgaggactct gcggtctatt tctgtgcaag a            291

<210> SEQ ID NO 25
<211> LENGTH: 290
<212> TYPE: DNA
<213> ORGANISM: Mus sp.

<400> SEQUENCE: 25
gtccagctgc agcagtctgg acctgagctg gtgaagcctg ggcttcagt gaagatgtcc    60 tgcaaggctt ctggctacac cttcacaagc tactatatac actgggtgaa gcagaggcct   120
ggacagggac ttgagtggat tggatggatt tatcctggag atggtagtac taagtacaat   180
gagaagttca aggcaaggac cacactgact gcagacaaat cctccagcac agcctacatg   240
ttgctcagca gcctgacctc tgaggactct gcgatctatt tctgtgcaag              290

<210> SEQ ID NO 26
<211> LENGTH: 288
<212> TYPE: DNA
<213> ORGANISM: Mus sp.

<400> SEQUENCE: 26
cagctgcagc agtctggacc tgagctggtg aagcctgggg cttcagtgaa gatatcctgc    60
aaggcttctg ctacaccttt cactgactac tatataaact gggtgaagca gaggcctgga   120
cagggacttg agtggattgg atggattttat cctggaagcg gtaatactaa gtacaatgag   180
aagttcaagg gcaaggccac attgactgta gacacatcct ccagcacagc ctacatgcag   240
ctcagcagcc tgacctctga ggactctgcg gtctattttct gtgcaaga               288
```

```
<210> SEQ ID NO 27
<211> LENGTH: 291
<212> TYPE: DNA
<213> ORGANISM: Mus sp.

<400> SEQUENCE: 27
gttcagctgc agcagtctgg acctgagctg gtgaagcctg ggctttagt gaagatatcc      60 tgcaaggctt ctggttacac cttcacaagc tacgatataa actgggtgaa gcagaggcct     120
ggacagggac ttgagtggat tggatggatt tatcctggag atggtagtac taagtacaat     180
gagaaattca gggcaaggc cacactgact gcagacaaat cctccagcac agcctacatg      240
cagctcagca gcctgacttc tgagaactct gcagtctatt tctgtgcaag a              291

<210> SEQ ID NO 28
<211> LENGTH: 291
<212> TYPE: DNA
<213> ORGANISM: Mus sp.

<400> SEQUENCE: 28
gtccagctgc agcagtctgg acctgagctg gtgaaacctg ggcttcagt gcggatatcc      60 tgcaaggctt ttgggtacac cttcacaagc tactatatac actgggtgaa gcagaggcct    120
ggacagggac ttgagtggat tggatggatt tatcctggaa atgttaatac taagtacaat    180
gagaagttca gggcaaggc cacactgact gcagacaaat cctccagcac agcctacatg     240
cagctcagca gcctgacctc tgaggactct gcggtctatt tctgtgcaag a              291

<210> SEQ ID NO 29
<211> LENGTH: 246
<212> TYPE: DNA
<213> ORGANISM: Mus sp.

<400> SEQUENCE: 29
tcagtgaaga tttcctgcaa agcttctggc tacgcattca gtagctactg gatgaactgg      60
gtgaagcaga ggcctggaaa gggtcttgag tggattggac agatttatcc tggagatggt    120
gatactaact acaacggaaa gttcaagggc aaggccacac tgactgcaga caaatcctcc    180
agcacagcct acatgcagct cagcagcctg acctctgagg actctgcggt ctatttctgt    240
gcaaga                                                                246

<210> SEQ ID NO 30
<211> LENGTH: 325
<212> TYPE: DNA
<213> ORGANISM: Mus sp.
<220> FEATURE:
<221> NAME/KEY: CDS
<222> LOCATION: (3)..(320)

<400> SEQUENCE: 30 tt ctg atg acc cag tct cct gct tcc tta gct gta tct ctg ggg cag        47
   Leu Met Thr Gln Ser Pro Ala Ser Leu Ala Val Ser Leu Gly Gln
   1               5                  10                  15 agg gcc acc atc tca tac agg gcc agc aaa agt gtc agt aca tct ggc        95
Arg Ala Thr Ile Ser Tyr Arg Ala Ser Lys Ser Val Ser Thr Ser Gly
             20                  25                  30 tat agt tat atg cac tgg aac caa cag aaa cca gga cag cca ccc aga       143
Tyr Ser Tyr Met His Trp Asn Gln Gln Lys Pro Gly Gln Pro Pro Arg
         35                  40                  45 ctc ctc atc tat ctt gta tcc aac cta gaa tct ggg gtc cct gcc agg       191
Leu Leu Ile Tyr Leu Val Ser Asn Leu Glu Ser Gly Val Pro Ala Arg
     50                  55                  60
```

```
ttc agt ggc agt ggg tct ggg aca gac ttc acc ctc aac atc cat cct        239
Phe Ser Gly Ser Gly Ser Gly Thr Asp Phe Thr Leu Asn Ile His Pro
 65                  70                  75 gtg gag gag gag gat gct gca acc tat tac tgt cag cac att agg gag        287
Val Glu Glu Glu Asp Ala Ala Thr Tyr Tyr Cys Gln His Ile Arg Glu
 80                  85                  90                  95 ctt aca cgt tcg gag ggg gga cca agc tgg aaa taaaa                      325
Leu Thr Arg Ser Glu Gly Gly Pro Ser Trp Lys
                100                 105
```

<210> SEQ ID NO 31
<211> LENGTH: 106
<212> TYPE: PRT
<213> ORGANISM: Mus sp.

<400> SEQUENCE: 31

```
Leu Met Thr Gln Ser Pro Ala Ser Leu Ala Val Ser Leu Gly Gln Arg
  1               5                  10                  15

Ala Thr Ile Ser Tyr Arg Ala Ser Lys Ser Val Ser Thr Ser Gly Tyr
                 20                  25                  30

Ser Tyr Met His Trp Asn Gln Gln Lys Pro Gly Gln Pro Pro Arg Leu
             35                  40                  45

Leu Ile Tyr Leu Val Ser Asn Leu Glu Ser Gly Val Pro Ala Arg Phe
         50                  55                  60

Ser Gly Ser Gly Ser Gly Thr Asp Phe Thr Leu Asn Ile His Pro Val
 65                  70                  75                  80

Glu Glu Glu Asp Ala Ala Thr Tyr Tyr Cys Gln His Ile Arg Glu Leu
                 85                  90                  95

Thr Arg Ser Glu Gly Gly Pro Ser Trp Lys
                100                 105
```

<210> SEQ ID NO 32
<211> LENGTH: 294
<212> TYPE: DNA
<213> ORGANISM: Mus sp.
<220> FEATURE:
<221> NAME/KEY: CDS
<222> LOCATION: (1)..(294)

<400> SEQUENCE: 32

```
gac att gtg ctg aca cag tct cct gct tcc tta gct gta tct ctg ggg        48
Asp Ile Val Leu Thr Gln Ser Pro Ala Ser Leu Ala Val Ser Leu Gly
  1               5                  10                  15 cag agg gcc acc atc tca tgc agg gcc agc aaa agt gtc agt aca tct        96
Gln Arg Ala Thr Ile Ser Cys Arg Ala Ser Lys Ser Val Ser Thr Ser
                 20                  25                  30 ggc tat agt tat atg cac tgg tac caa cag aaa cca gga cag cca ccc        144
Gly Tyr Ser Tyr Met His Trp Tyr Gln Gln Lys Pro Gly Gln Pro Pro
             35                  40                  45 aaa ctc ctc atc tat ctt gca tcc aac cta gaa tct ggg gtc cct gcc        192
Lys Leu Leu Ile Tyr Leu Ala Ser Asn Leu Glu Ser Gly Val Pro Ala
         50                  55                  60 agg ttc agt ggc agt ggg tct ggg aca gac ttc acc ctc aac atc cat        240
Arg Phe Ser Gly Ser Gly Ser Gly Thr Asp Phe Thr Leu Asn Ile His
 65                  70                  75                  80 cct gtg gag gag gag gat gct gca acc tat tac tgt cag cac agt agg        288
Pro Val Glu Glu Glu Asp Ala Ala Thr Tyr Tyr Cys Gln His Ser Arg
                 85                  90                  95 gag ctt                                                                294
Glu Leu
```

```
<210> SEQ ID NO 33
<211> LENGTH: 98
<212> TYPE: PRT
<213> ORGANISM: Mus sp.

<400> SEQUENCE: 33

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu

<210> SEQ ID NO 34
<211> LENGTH: 290
<212> TYPE: DNA
<213> ORGANISM: Mus sp.

<400> SEQUENCE: 34
ttgtgctaac acagtctcct gcttccttag ctgtatctct ggggcagagg gccaccatct      60
catgcagggc cagccaaagt gtcagtacat ctagctatag ttatatgcac tggtaccaac     120
agaaaccagg acagccaccc aaactcctca tcaagtatgc atccaaccta gaatctgggg     180
tccctgccag gttcagtggc agtgggtctg ggacagactt caccctcaac atccatcctg     240
tggaggagga ggatactgca acatattact gtcagcacag ttgggagatt                290

<210> SEQ ID NO 35
<211> LENGTH: 287
<212> TYPE: DNA
<213> ORGANISM: Mus sp.

<400> SEQUENCE: 35
ttgtgctgac ccaatctcca gcttctttgg ctgtgtctct agggcagagg gccaccatct      60
cctgcaaggc cagccaaagt gttgattatg atggtgatag ttatatgaac tggtaccaac     120
agaaaccagg acagccaccc aaactcctca tctatgctgc atccaatcta gaatctggga     180
tcccagccag gtttagtggc agtgggtctg ggacagactt caccctcaac atccatcctg     240
tggaggagga ggatgctgca acctattact gtcagcaaag taatgag                  287

<210> SEQ ID NO 36
<211> LENGTH: 36
<212> TYPE: DNA
<213> ORGANISM: Mus sp.

<400> SEQUENCE: 36
tacacgttcg gaggggggac caagctggaa ataaaa                                36

<210> SEQ ID NO 37
<211> LENGTH: 33
<212> TYPE: DNA
<213> ORGANISM: Mus sp.
```

<400> SEQUENCE: 37
acgttcggtg gaggcaccaa gctggaaatc aaa    33

<210> SEQ ID NO 38
<211> LENGTH: 287
<212> TYPE: DNA
<213> ORGANISM: Mus sp.

<400> SEQUENCE: 38
ttgtgctgac ccaatctcca gcttctttgg ctgtgtctct agggcagagg gccaccatat    60
cctgcagagc cagtgaaagt gttgatagtt atggcaatag ttttatgcac tggtaccagc    120
agaaaccagg acagccaccc aaactcctca tctatcttgc atccaaccta gaatctgggg    180
tccctgccag gttcagtggc agtgggtcta ggacagactt caccctcacc attgatcctg    240
tggaggctga tgatgctgca acctattact gtcagcaaaa taatgag    287

<210> SEQ ID NO 39
<211> LENGTH: 287
<212> TYPE: DNA
<213> ORGANISM: Mus sp.

<400> SEQUENCE: 39
ttgtgctgac ccaggcccct ccttccttgg atgtttctca agggtagagg gccaccatct    60
cctgcaggac cagcaaaagt gtcagaacat ctagctatag ttatatgcac tggtaccaac    120
agaaaccagg tcagccgccc aaactcctca atctatgtgc atccaaccaa gtatctaggg    180
tcccagccag gttcagtggc agtggatctg ggacagactt caccctcaaa atccatcctg    240
tggaggagga ggatgctgca acctatttct gtcagcaaag taatgag    287

<210> SEQ ID NO 40
<211> LENGTH: 287
<212> TYPE: DNA
<213> ORGANISM: Mus sp.

<400> SEQUENCE: 40
ttgtgctgac ccaatctcca gcttctttgg ctgtgtctct aggacagaga gccactatct    60
tctgcagagc cagccagagt gtcgattata atggaattag ttatatgcac tggttccaac    120
agaaaccagg acagccaccc aaactcctca tctatgctgc atccaaccta gaatctggga    180
tccctgccag gttcagtggc agtgggtctg ggacagactt caccctcaac atccatcctg    240
tggaggagga agatgctgca acctattact gtcagcaaag tattgag    287

<210> SEQ ID NO 41
<211> LENGTH: 287
<212> TYPE: DNA
<213> ORGANISM: Mus sp.

<400> SEQUENCE: 41
ttgtgctgac ccaatctcca gcttctttgg ctgtgtctct agggcagagg gccaccatat    60
cctgcagagc cagtgaaagt gttgatagtt atggcaatag ttttatgcac tggtaccagc    120
agaaaccagg acagccaccc aaactcctca tctatcgtgc atccaaccta gaatctggga    180
tccctgccag gttcagtggc agtgggtcta ggacagactt caccctcacc attaatcctg    240
tggaggctga tgatgttgca acctattact gtcagcaaag taatgag    287

```
<210> SEQ ID NO 42
<211> LENGTH: 290
<212> TYPE: DNA
<213> ORGANISM: Mus sp.

<400> SEQUENCE: 42
ttgtgctgac ccaatctcca gcttctttgg ctgtgtctct agggcagagg gccaccatct      60
cctgcagagc cagcgaaagt gttgataatt atggcattag ttttatgaac tggttccaac     120
agaaaccagg acagccaccc aaactcctca tctatgctgc atccaaccaa ggatccgggg     180
tccctgccag gtttagtggc agtgggtctg ggacagactt cagcctcaac atccatccta     240
tggaggagga tgatactgca atgtatttct gtcagcaaag taaggaggtt                290

<210> SEQ ID NO 43
<211> LENGTH: 286
<212> TYPE: DNA
<213> ORGANISM: Mus sp.

<400> SEQUENCE: 43
ttgtgctgac ccaatctcca gcttctttgg ctgtgtctct aggacagagg gccaccatat      60
cctgccaagc cagcgaaagt gtcagttttg ctggtacaag tttaatgcac tggtaccaac     120
agaaaccagg acagccaccc aaactcctca tctatcgtgc atccaaccta gaatctggag     180
tccctgccag gttcagtggc agtgggtctg agtcagactt cactctcacc atcgatcctg     240
tggaggaaga tgatgctgca atgtattact gtatgcaaag tatgga                   286

<210> SEQ ID NO 44
<211> LENGTH: 290
<212> TYPE: DNA
<213> ORGANISM: Mus sp.

<400> SEQUENCE: 44
ttgtgctcac ccaatctcca gcttctttgg ctgtgtctct agggcagaga gccaccatct      60
cctgcagagc cagtgaaagt gttgaatatt atggcacaag tttaatgcag tggtaccaac     120
agaaaccagg acagccaccc aaactcctca tctatgctgc atccaacgta gaatctgggg     180
tccctgccag gtttagtggc agtgggtctg ggacagactt cagcctcaac atccatcctg     240
tggaggagga tgatattgca atgtatttct gtcagcaaag taggaaggtt                290

<210> SEQ ID NO 45
<211> LENGTH: 5
<212> TYPE: PRT
<213> ORGANISM: Mus sp.

<400> SEQUENCE: 45

Arg Ser Trp Met Asn
1               5

<210> SEQ ID NO 46
<211> LENGTH: 17
<212> TYPE: PRT
<213> ORGANISM: Mus sp.

<400> SEQUENCE: 46

Arg Ile Tyr Pro Gly Asp Gly Asp Thr Asn Tyr Asn Gly Lys Phe Lys
1               5                   10                  15

Gly
```

```
<210> SEQ ID NO 47
<211> LENGTH: 14
<212> TYPE: PRT
<213> ORGANISM: Mus sp.

<400> SEQUENCE: 47

Ser Glu Leu Trp Ser Lys Met Phe Ala Tyr Trp Gly Gln Gly
1               5                   10

<210> SEQ ID NO 48
<211> LENGTH: 15
<212> TYPE: PRT
<213> ORGANISM: Mus sp.

<400> SEQUENCE: 48

Arg Ala Ser Lys Ser Val Ser Thr Ser Gly Tyr Ser Tyr Met His
1               5                   10                  15

<210> SEQ ID NO 49
<211> LENGTH: 7
<212> TYPE: PRT
<213> ORGANISM: Mus sp.

<400> SEQUENCE: 49

Leu Val Ser Asn Leu Glu Ser
1               5

<210> SEQ ID NO 50
<211> LENGTH: 8
<212> TYPE: PRT
<213> ORGANISM: Mus sp.

<400> SEQUENCE: 50

Ile Arg Glu Leu Thr Arg Ser Glu
1               5
```

MONOCLONAL ANTIBODIES AGAINST PCBP-1 ANTIGENS, AND USES THEREFOR

CROSS-REFERENCE TO RELATED APPLICATIONS

This application is a continuation of U.S. application Ser. No. 12/684,090, filed Jan. 7, 2010, which claims the benefit of U.S. Provisional Application No. 61/172,457, filed Apr. 24, 2009, and of U.S. Provisional Application No. 61/020,601, filed Jan. 11, 2009, both of which are hereby incorporated by reference in their entireties.

SEQUENCE LISTING

The Sequence Listing is hereby incorporated by reference in its entirety, including the file named P30912US.txt, which is 23,810 bytes in size and was created on Jan. 7, 2010, which is likewise herein incorporated by reference in its entirety.

BACKGROUND OF THE INVENTION

1. Field of the Invention

The present invention provides and includes monoclonal antibodies (MoAbs or mAbs) specific or preferentially selective for PCBP-1 antigens, hybridoma lines that secrete these PCBP-1 antibodies or antibody fragments, and the use of such antibodies and antibody fragments to detect PCBP-1 antigens, particularly those expressed by cancer cells. The present invention also includes antibodies that are specific for or show preferential binding to a soluble form of PCBP-1. The present invention further includes chimeric and humanized antibodies, processes for producing monoclonal, chimeric, and humanized antibodies using recombinant DNA technology, and their therapeutic uses, particularly in the treatment of cancer. The present invention further includes methods and kits for the immunodetection and immunotherapy of cells for samples which express PCBP-1 antigens.

2. Background

One human carcinoma tumor antigen is PCBP-1 (poly(rC) binding protein-1). Pcbp-1 is an intronless human gene reported to have been generated by retrotransposition of a fully processed PCBP-2 mRNA. It is also reported to be located on chromosome 2 (70.17-70.17 Mb). The protein encoded by the Pcbp-1 gene is a reported multifunctional protein. PCBP-1, along with PCBP-2 and hnRNPK, are reported to form the major cellular poly(rC)-binding protein. Pcbp-1 has been sequenced. See UniProt Q15365, Q53SS8, Q14975; OMIM 601209; NCBI Gene 5093; NCBI RefSeq NP_006187; NCBI RefSeq NM_006196, NP_006187; NCBI UniGene 5093; and NCBI Accession AK130439, AAA91317. Homologues of Pcbp-1 are also reported, including, but not limited to, homologues of Pcbp-1 in the mouse (see NCBI UniGene 23983; UniProt P60335; and NCBI RefSeq NM_011865, NP_035995), dog, and rat.

PCBP-1 has also been reported to regulate transcription from a few individual promoters, to be important for the metabolism and gene expression of HIV-1 and poliovirus, and to stimulate IRES-mediated translation initiation in vitro and in vivo (Mitchell et al., 2003). It has also been reported to be modestly increased in the epidermis of elderly individuals (Gromov et al., *Mol Cell Proteomics* 2(2):70-84, 2003, herein incorporated by reference in its entirety).

Accordingly, there is a need for an antibody molecule to selectively detect diseases characterized by the expression or localization of Pcbp-1 gene products. There is also a need for an antibody molecule which has affinity for particular gene products of Pcbp-1.

SUMMARY OF THE INVENTION

The present invention provides an antibody capable of binding to a soluble form of PCBP-1 with a specific affinity of between $10^{-8}$M and $10^{-11}$M.

The present invention also provides an antibody capable of binding to a soluble form of PCBP-1 in a cell.

The present invention also provides an antibody capable of selectively reducing the activity of a soluble PCBP-1 in a cell.

The present invention also provides an antibody capable of preferentially binding to a soluble form of a PCBP-1 antigen.

The present invention also provides an antibody capable of preferentially binding to a soluble form of a PCBP-1 antigen, wherein the preferential binding is relative to a membrane form of PCBP-1.

The present invention also provides a method of determining the status of a cell in a sample by (a) obtaining said sample; (b) contacting said sample with an antibody capable of preferentially detecting a soluble form of PCBP-1 antigen; and (c) determining quantity or localization of said antigen.

The present invention also provides an antibody specific for a PCBP-1 antigen, comprising the heavy chain CDR antigen binding site sequences CDR1 (SEQ ID NO: 45), CDR2 (SEQ ID NO: 46), and CDR3 (SEQ ID NO: 47) as set forth in FIG. 10, and the light chain CDR antigen binding site sequences CDR1 (SEQ ID NO: 48), CDR2 (SEQ ID NO: 49), and CDR3 (SEQ ID NO: 50) as set forth in FIG. 11.

The present invention also provides an antibody specific for a PCBP-1 antigen, comprising one or more of the heavy chain CDR antigen binding site sequences set forth in FIG. 10 (SEQ ID NOs: 45-47), and one or more of the light chain CDR antigen binding site sequences set forth in FIG. 11 (SEQ ID NOs: 48-50).

The present invention also provides an isolated DNA sequence which encodes the heavy chain of an antibody molecule, wherein said antibody molecule has specificity for PCBP-1 and wherein the variable domain of said heavy chain comprises a CDR having the antigen binding site sequences CDR1 (SEQ ID NO: 45), CDR2 (SEQ ID NO: 46), and CDR3 (SEQ ID NO: 47) set forth in FIG. 10.

The present invention also provides an isolated DNA sequence which encodes the light chain of an antibody molecule, wherein said antibody molecule has specificity for PCBP-1 and further wherein the variable domain of said light chain comprises a CDR having the antigen binding site sequences CDR1 (SEQ ID NO: 48), CDR2 (SEQ ID NO: 49), and CDR3 (SEQ ID NO: 50) set forth in FIG. 11.

The present invention also provides an immunoassay for detecting a PCBP-1 antigen which binds to a monoclonal antibody having the one or more of the heavy chain CDR antigen binding site sequences set forth in FIG. 10 (SEQ ID NOs: 45-47), and one or more of the light chain CDR antigen binding site sequences set forth in FIG. 11 (SEQ ID NOs: 48-50), comprising: (a) contacting said sample with an effective binding amount of an antibody specific for a PCBP-1 antigen, comprising the heavy chain CDR antigen binding site sequences CDR1, CDR2, and CDR3, selected from the group consisting of SEQ ID NO: 45, SEQ ID NO: 46, and SEQ ID NO: 47, and the light chain CDR antigen binding site sequences CDR1, CDR2, and CDR3, selected from the group consisting of SEQ ID NO: 48, SEQ ID NO: 49, and SEQ ID NO: 50; and (b) detecting said antigen by detecting the binding of the antibody to the PCBP-1 antigen. The present invention also provides an immunoassay for detecting a PCBP-1 antigen which binds to a monoclonal antibody having the one or more of the heavy chain CDR antigen binding site sequences set forth in FIG. 10 (SEQ ID NOs: 45-47), and one or more of the light chain CDR antigen binding site sequences set forth in FIG. 11 (SEQ ID NOs: 48-50), comprising: (a) contacting said sample with an effective binding amount of an antibody specific for a PCBP-1 antigen, comprising one or more of the heavy chain CDR antigen binding site sequences selected from the group consisting of SEQ ID NO: 45, SEQ ID NO: 46, and SEQ ID NO: 47, and one or more of the light chain CDR antigen binding site sequences selected from the group consisting of SEQ ID NO: 48, SEQ ID NO: 49, and SEQ ID NO: 50; and (b) detecting said antigen by detecting the binding of the antibody to the PCBP-1 antigen.

The present invention also provides a method for developing drugs useful in treating and/or diagnosing diseases characterized by the expression of gene products of Pcbp-1 and homologues thereof, comprising the steps of: identifying gene products expressed by Pcbp-1 and homologues thereof in a subject having a disease, and utilizing said gene products as biomarkers in the development and identification of drugs selected from the group consisting of PCBP-1 antibodies and antibody fragments, inhibiting peptides, siRNA, antisense oligonucleotides, vaccines, and chemical compounds, which specifically target said gene products.

The present invention also provides a method of determining the status of a cell in a sample comprising: (a) obtaining said sample from a patient; (b) contacting said sample with an antibody capable of preferentially detecting a soluble form of PCBP-1 antigen; and (c) determining the quantity of said antigen.

The present invention also provides a method of determining the status of a cell in a sample comprising: (a) obtaining said sample from a patient; (b) contacting said sample with an antibody capable of preferentially detecting a soluble form of PCBP-1 antigen; and (c) determining the localization of said antigen.

The present invention also provides an antibody capable of recognizing an epitope selected from the group consisting of SEQ ID NOs: 1-14, and fragments thereof.

The present invention also provides an antibody capable of preferentially binding to a secreted form of PCBP-1.

BRIEF DESCRIPTION OF THE DRAWINGS

FIG. 2. Plasma samples from breast cancer patients are subjected to ELISA analysis using an anti-PCBP-1 monoclonal antibody. The figures represent optical density (OD) values of plasma readings for PCBP-1 levels. P-values are derived using the Mann Whitney Test. Control and metastatic group showed a significant difference (p<0.001). Control and non-metastatic groups did not show a significant difference. There is a significant difference between non-metastatic and metastatic groups (p<0.001). P values are determined by comparison with controls by ANOVA. Data are representative of four independent experiments performed in triplicate.

FIG. 4. Cervical cells obtained from pap smears of healthy and cervical cancer patients are seeded and grown on glass slides. The cells are fixed with formalin (10% with 0.1% Triton-X), washed with PBS and stained with anti-PCBP-1 mouse monoclonal antibody. Cells are then labeled with a FITC-labeled secondary goat-anti-mouse antibody and subjected to laser confocal microscopy. Indirect immunofluorescent staining is observed in the cytoplasm and nucleus of normal cervical cells. Cervical cancer cells (CIN III) display cytoplasmic staining only.

FIG. 10 also discloses sequence for J558.18 (SEQ ID NO: 17); VMU-3.2 (SEQ ID NO: 19); J558.85.191 (SEQ ID NO: 20); JH3 (SEQ ID NO: 21); JE2 (SEQ ID NO: 22); J558.83.189 (SEQ ID NO: 23); J558.29 (SEQ ID NO: 24); J558.27 (SEQ ID NO: 25); J558.87.193 (SEQ ID NO: 26); VEA1 (SEQ ID NO: 27); J558.30 (SEQ ID NO: 28); and J558.18A (SEQ ID NO: 29) respectfully, in order of appearance.

FIG. 11 also discloses sequence for 21-12 SEQ ID NO: 32); 21-7 (SEQ ID NO: 34); 21-4 (SEQ ID NO: 35); JK2 (SEQ ID NO: 36); JK1 (SEQ ID NO: 37); 21-10 (SEQ ID NO: 38); 21-8 (SEQ ID NO: 39); 21-3 (SEQ ID NO: 40); 21-5 (SEQ ID NO: 41); 21-2 (SEQ ID NO: 42); 21-9 (SEQ ID NO: 43); 21-1 (SEQ ID NO: 44) respectfully, in order of appearance.

FIG. 12. Experimental mass, calculated mass and sequence of PCBP-1 regions (SEQ ID NOs. 1-14).

FIG. 13. Chart of PCBP-1 expression as detected by immunohistochemistry using Alper PCBP-1 mouse monoclonal antibody in normal vs. cancer tissues.

DETAILED DESCRIPTION

1. Definitions

Figure 1:
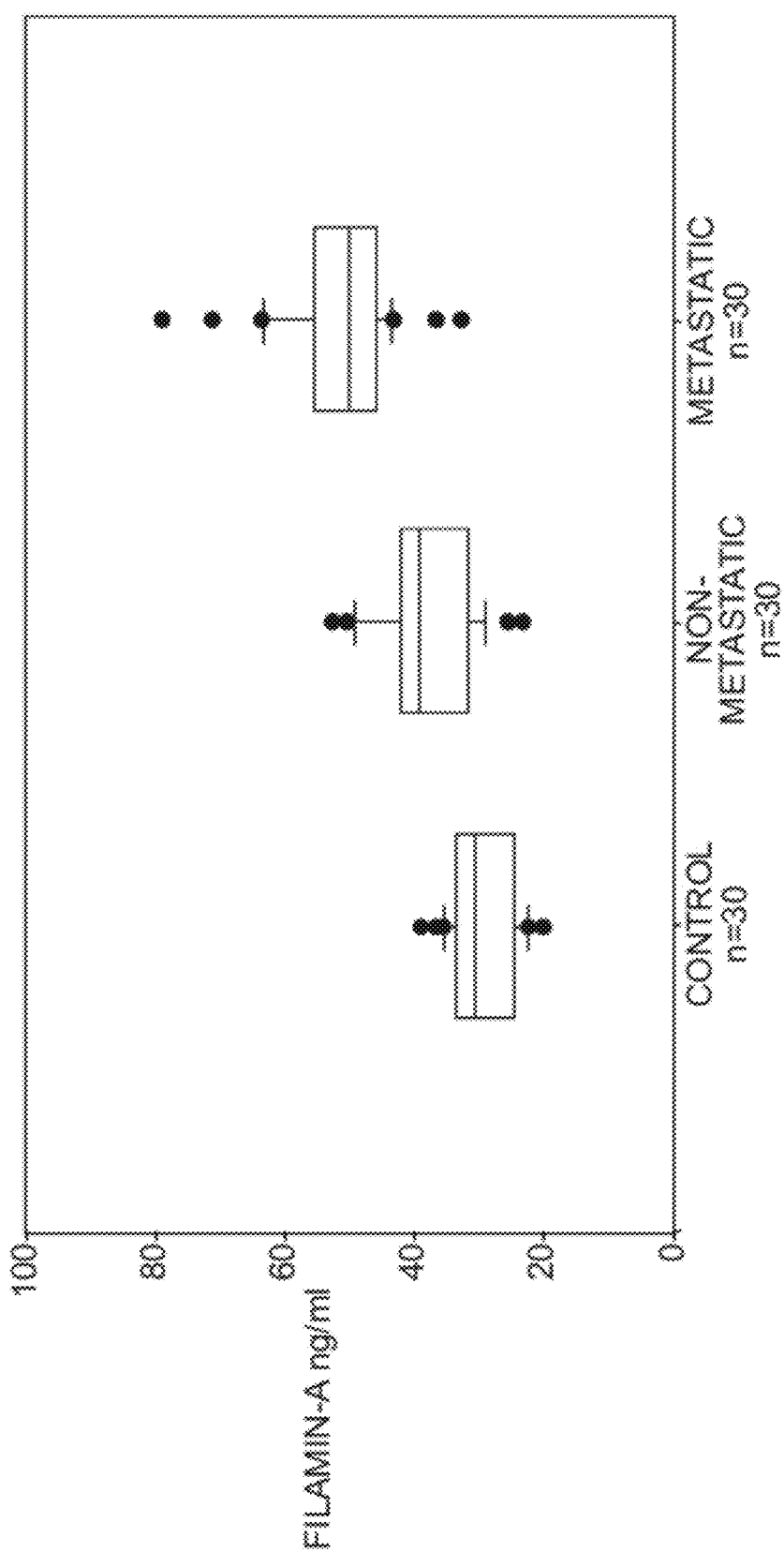
FIG. 1. Plasma filamin-A levels are measured with an enzyme-linked immunosorbent enzyme assay. The figures represent optical density (OD) values of plasma readings for filamin-A levels. P-values are derived using the Mann Whitney Test and show a significant difference among control, non-metastatic and metastatic groups (p<0.001). P values are determined by comparison with controls by ANOVA. Data are representative of four independent experiments performed in triplicate.

Antibody: This refers to single chain, two-chain, and multi-chain proteins and glycoproteins belonging to the classes of polyclonal, monoclonal, chimeric and hetero immunoglobulins (monoclonal antibodies being preferred); it also includes synthetic and genetically engineered variants of these immunoglobulins. "Antibody fragment" includes Fab, Fab', F(ab')$_2$, and Fv fragments, as well as any portion of an antibody having specificity toward a desired target epitope or epitopes.

Monoclonal Antibody: This refers to antibodies that are identical because they are produced by one type of immune cell that are all clones of a single parent cell. The monoclonal antibodies of the present invention can include intact monoclonal antibodies, antibody fragments, conjugates, or fusion proteins, which contain a $V_H$-$V_L$ pair where the CDRs form the antigen binding site.

Chimeric Antibody: This refers to an antibody which includes sequences derived from two different antibodies, which typically are of different species. Most typically, chimeric antibodies include human and non-human antibody fragments, generally human constant and non-human variable regions.

Humanized Antibody: This refers to an antibody derived from a non-human antibody, and a human antibody which retains or substantially retains the antigen-binding properties of the parent antibody but which is less immunogenic in humans.

Antibody Conjugates, Fusion Proteins, and Bispecific Antibodies: These refer to monoclonal antibodies conjugated by chemical methods with radionuclides, drugs, macromolecules, or other agents.

Antigen: This refers to a molecule or a portion of a molecule capable of being bound by an antibody which is additionally capable of inducing an animal to produce an antibody capable of binding to an epitope of that antigen. An antigen can have one or more than one epitope. The specific reaction referred to above is meant to indicate that the antigen will react, in a highly selective manner, with its corresponding antibody and not with the multitude of other antibodies which can be evoked by other antigens.

Epitope: This refers to that portion of any molecule capable of being recognized by, and bound by, an antibody. In general, epitopes consist of chemically active surface groupings of molecules, for example, amino acids or sugar side chains, and have specific three-dimensional structural characteristics as well as specific charge characteristics. The epitopes of interest for the present invention are epitopes comprising amino acids.

Complementarity Determining Region, or CDR: This refers to amino acid sequences which together define the binding affinity and specificity of the natural Fv region of a native immunoglobulin binding site. The light and heavy chains of an immunoglobulin each have three CDRs. By definition, the CDRs of the light chain are bounded by the residues at positions 30 and 34 (CDR1), 49 and 65 (CDR2), 75 and 88 (CDR3); the CDRs of the heavy chain are bounded by the residues at positions 22 and 36 (CDR1), 52 and 58 (CDR2), and 70 and 77 (CDR3), using the numbering convention delineated by Kabat et al., (1991) Sequences of Proteins of Immunological Interest, 5th Edition, Department of Health and Human Services, Public Health Service, National Institutes of Health, Bethesda (NIH Publication No. 91-3242).

Framework Region or FWR: This refers to amino acid sequences interposed between CDRs. These portions of the antibody serve to hold the CDRs in an appropriate orientation for antigen binding.

Specificity Determining Residue, or SDR: This refers to amino acid residues of an immunoglobulin that are directly involved in antigen contact.

Constant Region: This refers to the portion of the antibody molecule which confers effector functions. The heavy chain constant region can be selected from any of five isotypes: alpha, delta, epsilon, gamma or mu. Heavy chains of various subclasses (such as the IgG subclass of heavy chains) are responsible for different effector functions. Thus, by choosing the desired heavy chain constant region, humanized antibodies with the desired effector function can be produced. The light chain constant region can be of the kappa or lambda type, preferably the kappa type.

Immunogenicity: A measure of the ability of a targeting protein or therapeutic moiety to elicit an immune response (humoral or cellular) when administered to a recipient. The present invention is concerned with the immunogenicity of antibodies to PCBP-1.

Immunoreactivity: A measure of the ability of an immunoglobulin to recognize and bind to a specific antigen.

PCBP-1 Antibodies or PCBP-1 mAbs: This refers to antibodies specific to expression products of the PCBP-1 gene and homologues of the PCBP-1 gene, which can include antibodies specific to modified forms of the expression product that are produced by cancer cells. The antibodies include variants, such as chimeric, humanized, and other variants known to those skilled in the art. PCBP-1 antibodies are said to be specific for the PCBP-1 antigen if they exhibit preferential binding to the PCBP-1 antigen at least 85% of the time, at least 90% of the time, or, in a preferred aspect, at least 95% of the time. An example of such an antibody is Alper PCBP-1 mouse monoclonal antibody (7SK).

PCBP-1 Antigens: This refers to expression products generated by PCBP-1, which can be used as antigens, target molecules, biomarkers, or any combination thereof. The PCBP-1 antigens can be produced by the PCBP-1 gene and homologues of the PCBP-1 gene, and can include various modifications introduced by the cells expressing the PCBP-1 antigens, such as cancer cells.

Substantially Similar Binding Properties: This refers to a chimeric or humanized antibody or antibody fragment which retains the ability to specifically bind the antigen recognized by the parent antibody used to produce the chimeric antibody, humanized antibody, or antibody fragment. Preferably, the affinity of a chimeric antibody, humanized antibody, or antibody fragment is at least about 10% of the affinity of the parent antibody, more preferably at least about 25%, even more preferably at least about 50%. Most preferably, the chimeric antibody, humanized antibody, or antibody fragment exhibits antigen-binding affinity that is at least about 75% of the affinity of the parent antibody. Methods for assaying antigen-binding affinity are known in the art and include half-maximal binding assays, competition assays, and Scatchard analysis. In a preferred aspect, antigen-binding affinity is assayed using a competition assay. Such a comparison can be relative to Alper PCBP-1 mouse monoclonal antibody (7SK).

Substantially Homologous: Refers to immunoglobulin sequences that exhibit at least about 85% identity, more preferably about 90% identity, most preferably about 95% identity with a reference immunoglobulin, wherein % identity is determined by comparing the number identical of amino acid residues between the two immunoglobulins, wherein the positions of the amino acid residues are indicated using the Kabat numbering scheme.

Sameness for Monoclonal Antibody Products: For the purpose of determining sameness of monoclonal antibodies, and products thereof, the complementarity determining regions of the heavy and light chain variable regions are the principal molecular structural feature of a monoclonal antibody product. Two monoclonal antibodies can be considered the same if the amino acid sequences of the CDRs were the same, or if there were only minor amino acid differences between them. Whether differences in the amino acid sequences are minor can be determined by factors that include (but are not limited to) whether any particular residues have been established to be important for antigen binding. Amino acid differences outside the CDRs, or differences due to glycosylation patterns or post translational modifications do not result in different monoclonal antibodies. Changes in antibody structure that do not constitute differences between two monoclonal antibody products with the same CDRs include changes in the FWRs (i.e., humanizing a non-human derived monoclonal antibody or engineering certain framework residues that are important for antigen contact or for stabilizing the binding site, or changes in the constant region (i.e., changing the class or subclass of the constant region, changing specific amino acid residues which might alter an effector function, or changing the species from which the constant region is derived).

Substantially pure: For the purpose of the present invention, substantially pure refers to a homogeneous preparation preferably of PCBP-1 antibody or antibody fragment, or other chemical or biological agents. Substantially pure immunoglobulins of at least 80% homogeneity are preferred, with about 90% to about 95% homogeneity being more preferred, and 98% to 99% or more homogeneity is most preferred, and is generally considered acceptable for pharmaceutical uses.

2. Antibodies and Antibody Fragments

The present invention provides antibodies and antibody fragments specific for PCBP-1 antigens, including an antibody or antibody fragment capable of binding to a soluble form of PCBP-1 with a specific affinity of between $10^{-8}$ M and $10^{-11}$ M; an antibody or antibody fragment capable of binding to a soluble form of PCBP-1 in a cell; an antibody or antibody fragment capable of selectively reducing the activity of a soluble PCBP-1 in a cell; and an antibody or antibody fragment capable of preferentially binding to a soluble form of a PCBP-1.

An antibody or antibody fragment can be any antibody or antibody fragment and, without limitation, can be a monoclonal antibody, a chimeric antibody, a humanized antibody, or an antibody conjugate.

In an aspect, an antibody or antibody fragment can be any gamma globulin protein found in blood or other bodily fluids of vertebrates, and used by the host immune system to identify and neutralize foreign objects, such as bacteria and viruses. In one aspect, the antibody or antibody fragment can be selected from an antibody, a monoclonal antibody, a chimeric antibody, a humanized antibody, or an antibody conjugate. In an aspect, an antibody or antibody fragment can be any type of immunoglobulin protein, such as IgA, IgD, IgE, IgG or IgM.

In one aspect, an antibody or antibody fragment is capable of reducing the activity of PCBP-1. PCBP-1 activity is determined by measuring the poly(rC) binding of a sample. In an aspect, the poly(rC)-binding assay is carried out using a gel-shift assay as described in Ausubel FM, (1994). Current Protocols in Molecular Biology. Chichester: John Wiley and Sons ("Ausubel"), herein incorporated by reference in its entirety.

Antibodies or antibody fragments include those that are specific or preferentially selective for PCBP-1, and can be used to detect a soluble form of the PCBP-1 protein. A soluble PCBP-1 protein has a molecular weight of about 35-40 kDa, as measured by gradient polyacrylamide gel electrophoresis.

In one aspect of the present invention, an antibody or antibody fragment is capable of preferentially binding to a soluble form of PCBP-1 protein. In this aspect, such preferential binding PCBP-1 can be relative to any protein. In a particular aspect, such preferential binding to PCBP-1 is relative to PCBP-1 that is membrane bound or associated. In another particular aspect, such preferential binding to PCBP-1 is relative to PCBP-1 that is nuclear membrane bound or associated.

As used herein, a membrane associated protein is a protein that can be found localized with a membrane upon examination of cell. A membrane bound protein is one that interfaces at least in part with the lipid bilayer. In one aspect, it is bound to the membrane via ionic interactions. In another aspect, a membrane bound protein is bound to the membrane via covalent interactions. In a preferred aspect, a membrane bound protein is bound to the membrane via hydrogen bonds.

In an aspect of the present invention, the preferential binding is at least 2-fold, 3-fold, 4-fold, 5-fold, 10-fold, 100-fold, 1,000-fold, 10,000-fold or 1,000,000-fold. In another aspect, an antibody of the present invention preferentially binds a soluble form of PCBP-1 compared to a membrane form of PCBP-1. In a particular aspect, an antibody of the present invention preferentially binds a soluble form of PCBP-1 compared to a nuclear membrane form of PCBP-1, or the reverse, in another aspect. A binding of the antibody can be measured in any way, and a preferred methodology is a gel-shift assay, set forth in Ausubel.

In an aspect, an antibody or antibody fragment binds PCBP-1 or a particular form of PCBP-1 such as a soluble form or a membrane bound form with a specific affinity of greater than $10^{-7}M$, $10^{-8}M$, $10^{-9}M$, $10^{-10}M$, or $10^{-11}M$, between $10^{-8}M$-$10^{-11}M$, $10^{-9}M$-$10^{-10}M$, and $10^{-10}M$-$10^{-11}M$. In a preferred aspect, specific activity is measured using a competitive binding assay as set forth in Ausubel.

Antibodies and antibody fragments can optionally be immobilized on a solid phase, detectably labeled, or conjugated to a cytotoxic radionuclide, a cytotoxic drug, or a cytotoxic protein and the like.

Antibodies and antibody fragments of the present invention can target expression of PCBP-1 antigen by cells, preferably human cells, more preferably human cancer cells, and most preferably human breast, ovary, cervix, prostate, colon, stomach, kidney, liver, head, neck, lung, blood, pancreas, skin, testicle, thyroid and brain cancer cells. Expressed PCBP-1 antigens can include any form of the gene product, although particularly preferred aspects relate to the detection of the soluble or secreted form of PCBP-1. Such antigens can also include gene produced homologues of the Pcbp-1 gene and modified PCBP-1 antigens expressed by cancer cells.

Figure 10:
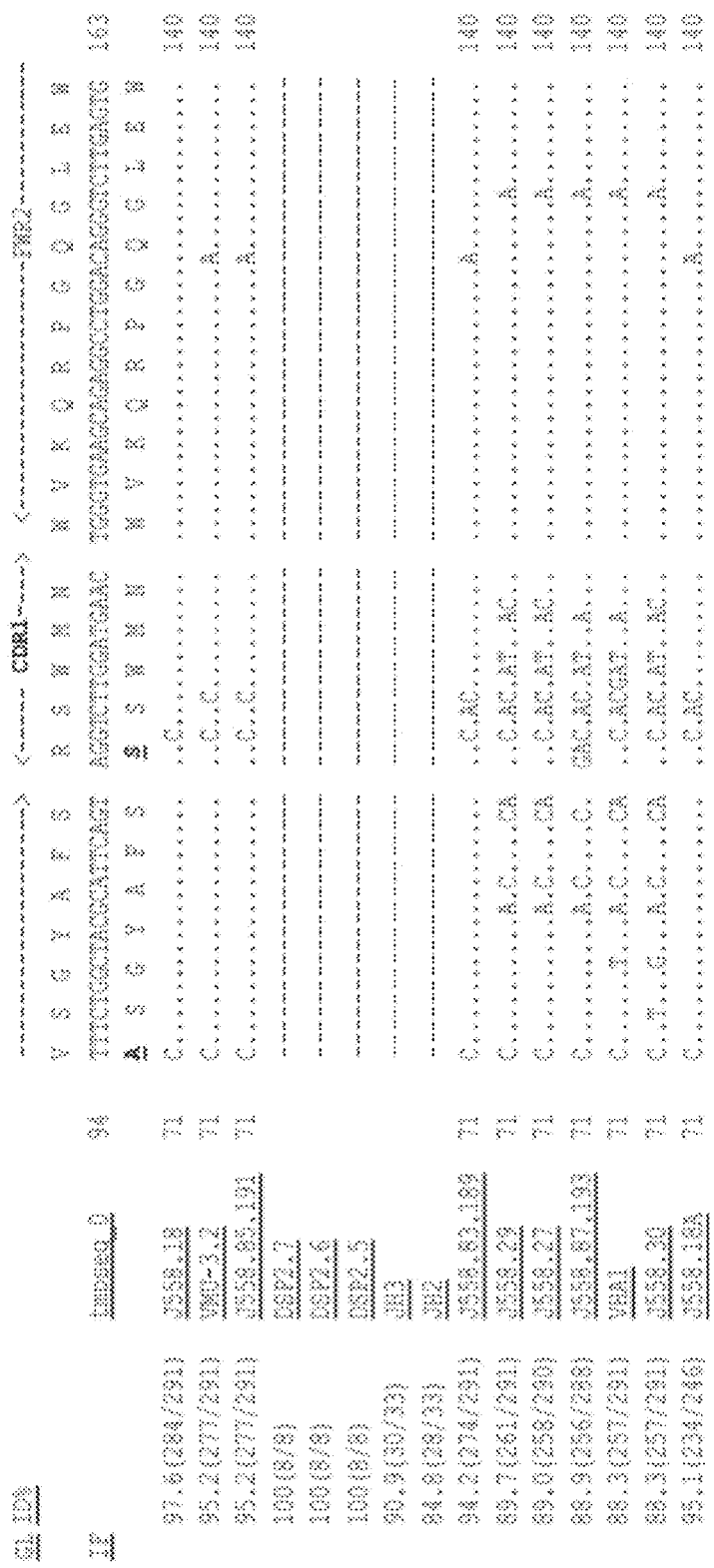
FIG. 10. FWRs and CDRs of the heavy chain of a PCBP-1 mAb (7SK), in which the polypeptide sequence provided in the top line (SEQ ID NO: 16) corresponds to the nucleotide sequence of a PCBP-1 mAb (SEQ ID NO: 15). Amino acid residues are numbered using the convention of Kabat et al., (1991) Sequences of Proteins of Immunological Interest, 5$^{th}$ Edition, Department of Health and Human Services, Public Health Service, National Institutes of Health, Bethesda (NIH Publication No. 91-3242). Bold residues set forth in underlined text indicate specificity determining residues (SDRs) (SEQ ID NO: 18).
Figure 11:
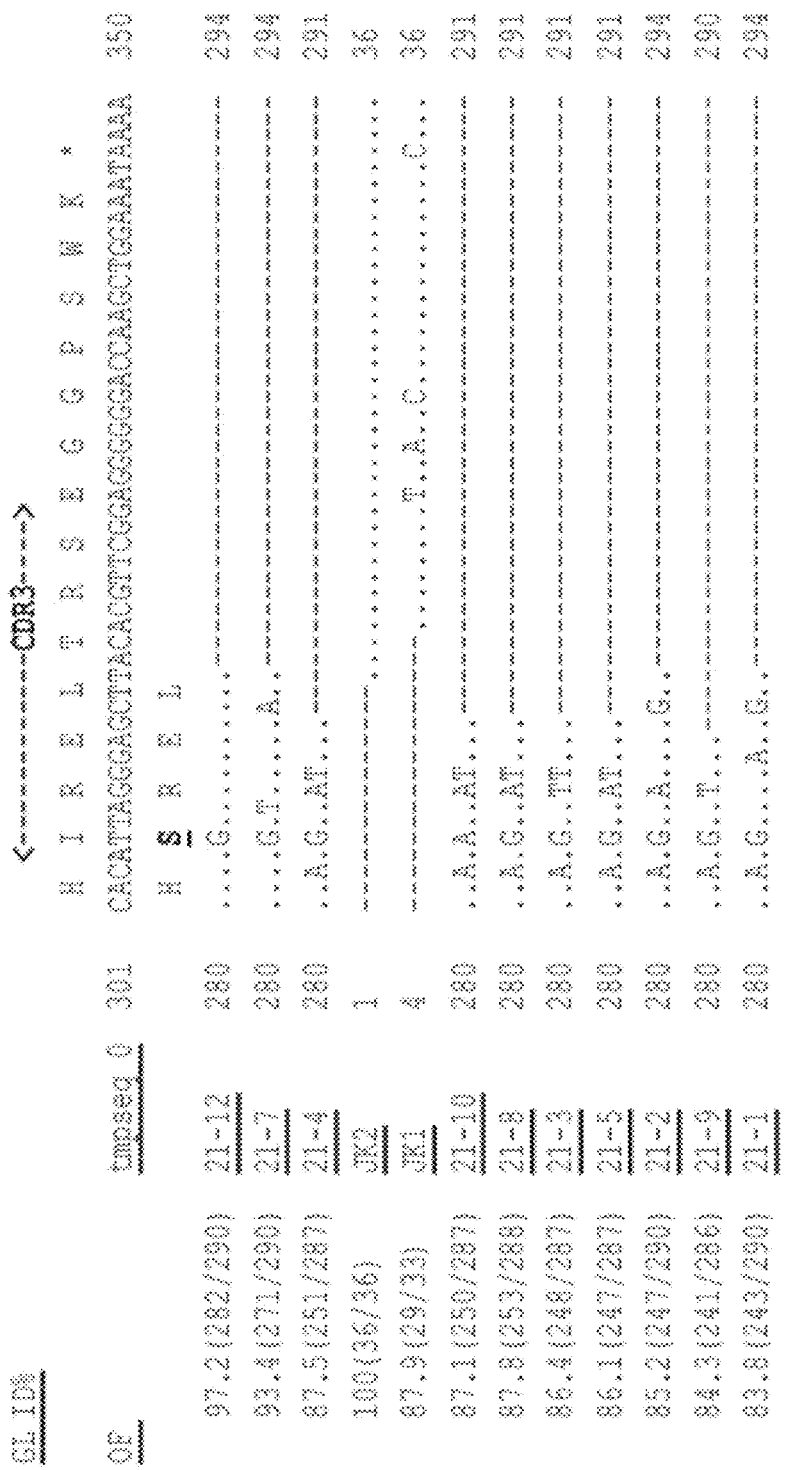
FIG. 11. FWRs and CDRs of the light chain of a PCBP-1 mAb (7SK), in which the polypeptide sequence provided in the top line (SEQ ID NO: 31) corresponds to the nucleotide sequence of a PCBP-1 mAb (SEQ ID NO: 30). Amino acid residues are numbered using the convention of Kabat et al. Bold residues set forth in underlined text indicate the specificity determining residues (SDRs) (SEQ ID NO: 33).

In an aspect, the present invention provides an antibody or antibody fragment specific for a PCBP-1 antigen, including the heavy chain CDR antigen binding site amino acid sequences CDR1 (SEQ ID NO: 45), CDR2 (SEQ ID NO: 46), and CDR3 (SEQ ID NO: 47) as set forth in FIG. 10, and the light chain CDR antigen binding site amino acid sequences CDR1 (SEQ ID NO: 48), CDR2 (SEQ ID NO: 49), and CDR3 (SEQ ID NO: 50) as set forth in FIG. 11. The present invention also provides an antibody specific for a PCBP-1 antigen, comprising one or more of the heavy chain CDR antigen binding site amino acid sequences set forth in FIG. 10 (SEQ ID NOs: 45-47), and one or more of the light chain CDR antigen binding site amino acid sequences set forth in FIG. 11 (SEQ ID NOs: 48-50).

The present invention includes PCBP-1 antibodies or antibody fragments having antigen binding sites CDR1 (SEQ ID NO: 45), CDR2 (SEQ ID NO: 46), and CDR3 (SEQ ID NO: 47), both heavy and light chains, as described in FIGS. 10 and 11. The invention also includes antibodies and antibody fragments specific to PCBP-1 expression products that contain antigen binding sites that are substantially homologous to these, or that result in substantially similar binding properties. The present invention also includes new hybridoma lines, and the monoclonal antibody molecules that they secrete, which are specific to PCBP-1 antigen expressed by normal or cancer cells. The present invention also includes chimeric and humanized antibodies and antibody fragments and also includes other modified antibodies and antibody fragments.

In addition to the specific amino acid sequences of the antigen binding sites of the heavy and light chains set forth in FIGS. 10 and 11, the present invention also encompasses antibodies and antibody fragments that are specific to PCBP-1 but which have FWR and/or CDR antigen binding site nucleotide sequences that are not identical to those set forth in FIGS. 10 and 11 (SEQ ID NOs: 19-29 and 34-44). Such antibodies and antibody fragments are preferred if they are specific or preferentially selective for the PCBP-1 antigen, preferably at least 85% as specific, more preferably at least 90% as specific, and most preferably at least 95% as specific for the PCBP-1 antigen as the antibody or antibody fragment of the present invention. According to a preferred aspect, a variant of an antibody or antibody fragment of the present invention can be as specific for the PCBP-1 antigen as a non-variant antibody or antibody fragment of the present invention, or can be more specific.

Antibodies and antibody fragments that are specific to PCBP-1 but which have FWR and/or CDR antigen binding site amino acid sequences that are not identical to those set forth in FIGS. 10 and 11 can possess the same or different specificity determining regions (SDRs) as the FWRs and/or CDRs of FIGS. 10 and 11 (SEQ ID NOs: 17 and 32) are included (set forth in bold, underlined text in these figures).

Modifications to the amino acid sequences of the antigen binding sites CDR1 (SEQ ID NO: 45 and 48, respectively), CDR2 (SEQ ID NO: 46 and 49, respectively), and CDR3 (SEQ ID NO: 47 and 50, respectively) set forth in FIG. 10 (heavy chain) and FIG. 11 (light chain) can occur in either or both of the FWR and CDR sequences. According to certain aspects of the invention, variations in antibodies or antibody fragments can occur where they have substantially homologous amino acid sequences, antibodies having substantially similar binding properties, or both.

Humanized variants of the antibodies or antibody fragments of the invention can contain a reduced murine content, and potentially, reduced immunogenicity, when compared to the murine antibodies or antibody fragments. Humanized variants include those that retain a binding affinity that is substantially similar to that of the original antibody or antibody fragment. An aspect of the invention provides CDR variants of humanized PCBP-1 antibodies or antibody fragments in which 1, 2, 3, 4, 5, or 6 (three heavy chain and three light chain) CDRs are humanized. A second aspect of the invention provides SDR variants of humanized PCBP-1 antibodies and antibody fragments in which only Specificity Determining Regions (SDRs) of at least one CDR from the PCBP-1 antibodies and antibody fragments are present in the humanized antibodies. The SDRs are selected from Table 1 or Table 2.

TABLE 1

Specificity-Determining Residues in Alper PCBP-1 Mouse Monoclonal Antibody Heavy Chain (SEQ ID NO: 17)

| Position | Residue |
|---|---|
| −1 | Q |
| 4 | Q |
| 5 | Q |
| 23 | A |
| 30 | S |

TABLE 2

Specificity-Determining Residues in Alper PCBP-1 Mouse Monoclonal Antibody Light Chain (SEQ ID NO: 32)

| Position | Residue |
|---|---|
| −2 | D |
| −1 | I |
| 1 | V |
| 2 | L |
| 21 | C |
| 38 | Y |
| 47 | K |
| 53 | A |
| 93 | S |

CDR variants can be formed by replacing at least one CDR of humanized PCBP-1 antibodies and antibody fragments with a corresponding CDR from a human antibody. CDR variants in which one, two, three, four, five, or six CDRs are replaced by a corresponding CDR from a human antibody and retain biological activity that is substantially similar to the binding affinity of the parental PCBP-1 mAb. CDR variants of the invention can have a binding affinity that is at least 25% of the binding affinity of the parental PCBP-1 antibody or antibody fragment, more preferably at least 50%, most preferably at least 75% or 90%.

CDR variants that have altered immunogenicity when compared to PCBP-1 antibodies and antibody fragments can be formed by grafting all six (three heavy chain and three light chain) CDRs from the PCBP-1 antibodies and antibody fragments of the present invention onto the variable light ($V_L$) and variable heavy ($V_H$) frameworks of human antibodies and antibody fragments. However, less than all six of the CDRs of the PCBP-1 antibodies and antibody fragments of the present invention can be present, while still permitting the humanized antibody to retain activity. Residues that are directly involved in antigen contact, the Specificity Determining Residues (SDRs), can be refined. SDR variants are formed by replacing at least one SDR of the PCBP-1 antibody or antibody fragment with a residue at a corresponding position from a human antibody. It should be noted that not all CDRs include SDRs.

In a preferred aspect, the variants of the present antibodies and antibody fragments include a combination of CDR and/or SDR substitutions to generate variants having reduced immunogenicity and a binding affinity that is substantially similar to that of the parental antibody or antibody fragment to PCBP-1.

In addition to variants specifically described herein, other "substantially homologous" modified immunoglobulins can be readily designed and manufactured using various recombinant DNA techniques. For example, the framework regions (FWRs) can be varied at the primary structure level. Moreover, a variety of different human framework regions can be used singly or in combination as a basis for the variant. In general, modifications of the genes can be readily accomplished by a variety of techniques, such as site-directed mutagenesis.

Alternatively, polypeptide fragments comprising only a portion of the primary antibody structure can be produced wherein the fragment substantially retains the immunoreactivity properties of the variant. Such polypeptide fragments include fragments produced by proteolytic cleavage of intact antibodies or fragments produced by inserting stop codons at the desired locations nucleotide sequence using site-directed mutagenesis. Single chain antibodies and fusion proteins which include at least an immunoreactivity fragment of the variant are also included within the scope of the invention.

The antibodies and their variants in accordance with the present invention can be directly or indirectly attached to effector moieties having therapeutic activity. Suitable effector moieties include cytokines, cytotoxins, radionuclides, drugs, immunomodulators, therapeutic enzymes, anti-proliferative agents, etc. Methods for attaching antibodies to such effectors are known in the art. These conjugated antibodies can be incorporated into any composition, including pharmaceutical compositions for use in treating diseases characterized by the expression of PCBP-1, including cancer, such as cancer of the breast, ovary, cervix, prostate, colon, stomach, kidney, liver, head, neck, lung, blood, pancreas, skin, testicle, thyroid and brain. The pharmaceutical compositions are preferably administered to a mammal, more preferably a human patient in need of such treatment, in order to treat the disease.

Antibodies and antibody fragments can either be labeled or unlabeled. Unlabeled antibodies can be used in combination with other labeled antibodies (second antibodies) that are reactive with the humanized antibody, such as antibodies specific for human immunoglobulin constant regions. Alternatively, the antibodies can be directly labeled. A wide variety of labels can be employed, such as radionuclides, fluors, enzymes, enzyme substrates, enzyme cofactors, enzyme inhibitors, ligands (particularly haptens), etc. Numerous types of immunoassays are available.

3. Nucleic Acid Molecules and Host Cells

Any of the antibodies or antibody fragments of the present invention can be encoded by nucleic acids. The present invention includes such molecules, fragments of such molecules and such molecules included in vectors and the like. Nucleic acid molecules also include the complement of such nucleic acid molecules. Both DNA and RNA molecules are examples of nucleic acid molecules.

In another aspect, the present invention provides an isolated DNA sequence which encodes the heavy chain of an antibody molecule, wherein said antibody molecule has specificity for PCBP-1 antigens and wherein the variable domain of said heavy chain comprises a CDR having the antigen binding site amino acid sequences CDR1, CDR2, and CDR3 set forth in FIG. 10.

In yet another aspect, the present invention provides an isolated DNA sequence which encodes the light chain of an antibody molecule, wherein said antibody molecule has specificity for PCBP-1 antigens and further wherein the variable domain of said light chain comprises a CDR having the antigen binding site amino acid sequences CDR1, CDR2, and CDR3 set forth in FIG. 11.

In another aspect, the present invention includes and provides a nucleic acid molecule in a host cell. Such nucleic acid molecule can be integrated into the genome of the host cell or can be present on a vector such as a plasmid or viral vector. A nucleic acid molecule may be transiently present in such a host cell. In one aspect, a host cell is selected from the group *E. coli*; Bacilli, including *Bacillus subtilis*; enterobacteriacae, including *Salmonella, Serratia* and *Psesudomonas*, yeast, including *Saccharomyces; Pichia pastoris*; Sf9 insect cells; Sp2/0, VERO and HeLa cells, Chinese hamster ovary (CHO) cell lines; W138, BHK, COS-7 and MDCK cell lines. In one aspect, a host cell is selected from a breast cancer cell line such as SKBR3, MCF-7, MDA-MB-231, MDA-MB-435, and ZR75B cells. In another aspect, a host cell is selected from a prostate cancer cell line such as PC3, DU145 and LNCap cells.

4. Methods of Making PCBP-1 Antibodies or Antibody Fragments

PCBP-1 antibodies or antibody fragments of the present invention can be developed, for example, using the human breast cancer cell line SKBR3 (available from the American Type Culture Collection as ATCC No. HTB30).

The present invention includes processes for producing monoclonal, chimeric, including humanized antibodies using recombinant DNA technology. See, for example, *Antibodies, A Laboratory Manual* (Harlow & Lane Eds., Cold Spring Harbor Press, 1988), which is herein incorporated by reference in its entirety.

PCBP-1 antibodies or antibody fragments of the present invention can be produced by any known method including, without limitation, generating murine hybridomas which produce antibodies or antibody fragments specific for PCBP-1. Hybridomas can be formed, for example, by the fusion of a mouse fusion partner cell and spleen cells from mice immunized against PCBP-1. Mice can be immunized with crude or semi-purified preparations containing the antigens of interest. To immunize the mice, a variety of different conventional protocols can be followed. For example, mice can receive primary and boosting immunizations of antigenic preparations.

Cell fusions can be accomplished by any procedures known to those skilled in the field of immunology. Fusion partner cell lines and methods for fusing and selecting hybridomas and screening for antibodies or antibody fragments are known.

Antibodies or antibody fragments of the present invention can be produced in large quantities, for example, by injecting hybridoma cells secreting the antibody into the peritoneal cavity of mice and, after appropriate time, harvesting the ascites fluid which contains a high titer of the antibody or antibody fragment, and isolating the antibody or antibody fragment therefrom. Alternatively, the antibodies and antibody fragments can be produced by culturing hybridoma cells in vitro and isolating the secreted antibody or antibody fragment from the cell culture medium.

PCBP-1 antibodies or antibody fragments of the present invention can also be produced by expressing the appropriate DNA sequence in a host after the sequence has been operably linked to an expression control sequence. Such expression vectors are often replicable in a host organism either as episomes or as an integral part of the host chromosomal DNA. Expression vectors often contain expression control sequences compatible with the host cell, such as an origin of replication. In addition, an expression vector can include a promoter to control expression of the gene, optionally, with operator sequences, and have ribosome binding site sequences and the like for initiating and completing transcription and translation. Suitable promoters include, without limitation, the polyhedrin promoter, lactose promoter system, a tryptophan promoter system, a beta-lactamase promoter system, or a promoter system from phage lambda. Expression vectors can also contain selection markers. DNA sequences encoding the light chain and heavy chain of the PCBP-1 antibodies and antibody fragments can be inserted into separate expression vectors, or into the same expression vector.

Suitable hosts include, without limitation, prokaryotic strains such as *E. coli*; Bacilli, including *Bacillus subtilis*; enterobacteriacae, including *Salmonella, Serratia* and *Psuedomonas*. Suitable hosts also include eukaryotic hosts such as yeast, including *Saccharomyces; Pichia pastoris*; Sf9 insect cells; Sp2/0, VERO and HeLa cells, Chinese hamster ovary (CHO) cell lines; W138, BHK, COS-7 and MDCK cell lines. Other suitable hosts can also be used in accordance with known expression techniques.

The vectors containing the DNA segments of interest can be transferred into the host cell by any method, which varies depending on the type of cellular host. For example, calcium chloride transfection, calcium phosphate treatment, electroporation or cationic liposome mediated transfection (such as DOTAP). Successfully transformed cells, can be identified by a variety of techniques for detecting the binding of a receptor to a ligand.

Expressed gene products can be purified according to any method, including, without limitation, ammonium sulfate precipitation, affinity columns, column chromatography, and gel electrophoresis. Substantially pure immunoglobulins of at least 80% homogeneity are preferred, with about 90% to about 95% homogeneity being more preferred, and 98% to 99% or more homogeneity is most preferred, and is generally considered acceptable for pharmaceutical uses.

Isolated or purified DNA sequences can be incorporated into a cloning or expression vector, which can in turn be used to transform a host cell. The transformed host cells can be used in a process for the production of an antibody molecule having specificity for PCBP-1 antigens, including culturing the host cells and isolating the antibody molecules they produce.

5. Diagnostic Methods, Assays, and Kits

In a further aspect, the present invention provides an immunoassay for detecting a PCBP-1 antigen comprising an antibody or antibody fragment of the present invention.

The present invention also provides an immunoassay for detecting a PCBP-1 antigen which binds to a monoclonal antibody having one or more of the heavy chain CDR antigen binding site amino acid sequences set forth in FIG. 10 (SEQ ID NOs: 45-47), and one or more of the light chain CDR antigen binding site amino acid sequences set forth in FIG. 11 (SEQ ID NOs: 48-50).

Such immunoassays can be used in any suitable manner, including, without limitation, by comprising: (a) contacting said sample with an effective binding amount of one of the antibodies or antibody fragments of the invention; and (b) detecting said antigen by detecting the binding of the antibody to the PCBP-1 antigen. Immunoassays of the present invention can be used to detect cancer cells expressing a PCBP-1 antigen, particularly cancer, tumor, carcinoma cells or neoplastic disease cells selected from the group consisting of breast, ovarian, cervical, prostate, colon, stomach, kidney, liver, head, neck, lung, blood, pancreatic, skin, testicular, thyroid and brain cancers.

In a further aspect, the present invention provides a kit for the immunohistochemical detection of carcinoma comprising: (a) a antibody or antibody fragment of the present invention; and (b) a secondary antibody conjugated to a detectable label.

In a further aspect, the present invention provides a kit for the immunohistochemical detection of carcinoma comprising: (a) a monoclonal antibody having one or more of the heavy chain CDR antigen binding site amino acid sequences set forth in FIG. 10, and one or more of the light chain CDR antigen binding site amino acid sequences set forth in FIG. 11; and (b) a secondary antibody conjugated to a detectable label.

Kits can include reagents for assaying a sample for a PCBP-1 antigen, where such kits may include: PCBP-1 antigen specific affinity reagents, such as an antibody, or fragment or mimetic thereof, and/or immunoassay devices comprising the same members of a signal producing system, such as antibodies, enzyme substrates, and the like; various buffers for use in carrying out the subject detection assays; a reference for determining the amount of a PCBP-1 antigen in a sample; and the like. Other examples of kits or kit formats are found in Alper, US Publication No. 2008/0293162, herein incorporated by reference in its entirety.

In further aspect, the present invention provides a method for diagnosing cancer in humans comprising: (a) removing a specimen from a patient suspected of having a cancer; (b) contacting the specimen with an antibody or antibody fragment of the present invention; (c) labeling the specimen; and (d) detecting the presence of the antigen-antibody complex by the label. Such a method of diagnosing cancer can be performed in vivo or in vitro.

In a still further aspect, the present invention provides a method for diagnosing cancer in humans comprising: (a) removing a specimen from a patient suspected of having a cancer; (b) contacting the specimen with a monoclonal antibody having one or more of the heavy chain CDR antigen binding site amino acid sequences set forth in FIG. 10, and one or more of the light chain CDR antigen binding site amino acid sequences set forth in FIG. 11; (c) labeling the specimen; and (d) detecting the presence of the antigen-antibody complex by the label. The method of diagnosing cancer can be performed in vivo or in vitro.

The cancer being diagnosed include those that are selected from the group consisting of solid tumors of the breast, ovary, cervix, prostate, colon, stomach, kidney, liver, head, neck, lung, pancreas, skin, testicle, thyroid and brain. In an additional aspect, the present invention provides a method for developing drugs useful in treating, diagnosing, or both treating and diagnosing diseases characterized by the expression of gene products of Pcbp-1 and homologues thereof, including identifying gene products expressed by Pcbp-1 and homologues thereof, and utilizing said gene products as biomarkers in the development and identification of drugs selected from the group consisting of PCBP-1 antibodies and antibody fragments, inhibiting peptides, siRNA, antisense oligonucleotides, vaccines, and chemical compounds, which specifically target said gene products.

An antibody or antibody fragment of the present invention can also be used in diagnosis of diseases characterized by the expression of PBCP-1, such as cancer. For example, in vivo diagnosis and imaging of a solid tumor of the breast, ovary, cervix, prostate, colon, stomach, kidney, liver, head, neck, lung, blood, pancreas, skin, testicle, thyroid and brain that expresses PBCP-1 can be performed in accordance with the methods of the invention. An antibody or antibody fragment of the present invention can also be used for diagnosis in vitro, for example, by using an antibody or antibody fragment to detect the presence of the cancer marker PBCP-1 in a fluid or tissue sample.

Antibodies and antibody fragments can be used in immunoassays to screen body fluids, such as serum, sputum, effusions, urine, cerebrospinal fluid, and the like, for the presence of PCBP-1. Antibodies and antibody fragments can be used for scanning or radioimaging, when labeled with an appropriate radiolabel, to detect primary or metastatic foci of tumor cells. Furthermore, the antibodies are useful in lymphoscintigraphy to detect lymph node involvement in the disease.

In one aspect, an antibody or antibody fragment of the present invention can be used to detect an increase in PCBP-1 expression. In another aspect, an antibody or antibody fragment of the present invention can be used to detect a decrease in PCBP-1 expression. In another aspect, an antibody or antibody fragment of the present invention can be used to detect a change in the cellular localization of PCBP-1. A PCBP-1 antibody or antibody fragment, which can include any or all of the antibodies or antibody fragments specific for PCBP-1-related gene products, and/or chimeric, humanized, or other variants thereof, can be used therapeutically, or in developing and performing assays, in vivo or in vitro diagnostic procedures, and imaging. The antibodies can be used alone or in combination with a pharmaceutically-acceptable or diagnostic carrier formulation. PCBP-1 antibodies or antibody fragments can be incorporated into a pharmaceutically or diagnostically acceptable, non-toxic, sterile carrier as a suspension or solution. They can be used as separately administered compositions or given in conjunction with chemotherapeutic or immunosuppressive agents.

The present invention provides therapeutic and diagnostic compositions comprising an antibody or antibody fragment of the present invention in combination with a pharmaceutically acceptable excipient, diluent or carrier. The present invention also includes a process for preparation of a therapeutic or diagnostic composition comprising admixing an antibody molecule of the present invention together with a pharmaceutically acceptable excipient, diluent or carrier. An antibody molecule can be the sole active ingredient in the therapeutic or diagnostic composition, or can be accompanied by other active ingredients including other antibody ingredients, for example anti-T cell, anti-IFNγ or anti-LPS antibodies, or non-antibody ingredients such as xanthines. Compositions can be incorporated into kits for diagnosing or treating diseases characterized by the expression of PCBP-1, including, without limitation, solid tumors, and particularly solid tumors of the breast, ovary, cervix, prostate, colon, stomach, kidney, liver, head, neck, lung, pancreas, skin, testicle, thyroid and brain.

Antibodies or antibody fragments of the present invention are useful for immunoassays which detect or quantitate PCBP-1 or cells bearing PCBP-1 in a sample. Such an immunoassay typically comprises incubating a biological sample in the presence of a detectably labeled antibody of the present invention capable of identifying the tumor antigen, and detecting the labeled antibody which is bound in a sample.

In an aspect of the present invention the level, localization or both of one or more forms of PCBP-1 can determine, confirm or indicate the status of a cell, collection of cells, sample from a subject. As used herein, "confirm" means that based on the level, localization or both of one or more forms of PCBP in a cell, collection of cells or sample, subject etc provides a sufficient basis to characterize the status of a cell, collection of cells, sample or subject etc. As used herein, "confirm" means that based on the level, localization or both of one or more forms of PCBP in a cell, collection of cells or sample, subject etc provides in combination with other analysis a basis to characterize the status of a cell, collection of cells, sample or subject etc. As used herein, "indicate" means that based on the level, localization or both of one or more forms of PCBP in a cell, collection of cells or sample, subject etc provides that more likely than not or greater probability of determining the status of a cell, collection of cells, sample or subject etc. is of a particular status A status of a cell or collection of cells can include any aspect and in one aspect is whether that a cell, collection of cells, sample, etc. are metastatic, non-metastatic tumor cells or normal cells. A status of a subject can include whether the analysis provides information on whether a metastatic cancer or non-metastatic tumor is present in the subject.

Examples of confirmatory analysis, assays, tests etc. that can be used to confirm or in combination with those disclosed include, without limitation, those set forth in Alper, US Publication No. 2008/0293162 (herein incorporated by reference in its entirety) as well as histological examination of samples.

In an aspect of the present invention the level, localization or both of one or more forms of PCBP-1 is diagnostic or prognostic of a disease or outcome probability.

In an aspect of the present invention a reduced level of a soluble form of PCPB-1 in a cell, collection of cells or sample can diagnose, prognose, monitor, determine, confirm or indicate that such derived is from a metastatic tissue. In one aspect, "reduced" can mean reduced relative to a control, with the control being a normal cell of the same type that is non-metastatic.

In this aspect, the reduction can be greater than 10, 20, 30, 40, 50, 60, 70, 80, 90, 95, or 99%. In another aspect, the reduction can be two-, four-, ten-, or twenty-fold or more.

In an aspect of the present invention an increased level of a soluble form of PCPB-1 in a cell, collection of cells or sample can diagnose, prognose, monitor, determine, confirm or indicate that such derived is from a metastatic tissue. In one aspect, "increased" can mean increased relative to a control, with the control being a normal cell of the same type that is non-metastatic. In this aspect, the increase can be greater than 10, 20, 30, 40, 50, 60, 70, 80, 90, 95, or 99%. In another aspect, the increase can be two-, four-, ten-, or twenty-fold or more.

In one aspect of the present invention, PCBP-1 expression is measured using immunohistochemistry followed by a quantitative method. In one aspect, a quantitative method can be software such as AQUANALYSIS™ software (manual is herein incorporated by reference in its entirety) (HistoRx, Inc., New Haven, Conn., USA). In another aspect, a quantitative method such as AQUANALYSIS™ software can be used in addition to the methods described in Example 13.

In one aspect of the present invention, PCBP-1 expression is relative to PCBP-1 expression in normal controls. In another aspect, PCBP-1 expression in cancer cells can be expressed as a percentage of PCBP-1 expression in normal controls. Statistical significance of differences in PCBP-1 expression can be measured using the Student's t-test. In one aspect, t=0.99. In another aspect, t=0.95. In another aspect, t=0.90.

In one aspect of the present invention, "strong expression" of PCBP-1 can be at least a 3-fold, 4-fold, 5-fold or greater increase in PCBP-1 expression as compared to normal tissues. In another aspect, "moderate expression" of PCBP-1 can be at least a 2- to 3-fold increase in PCBP-1 expression as compared to normal tissues. In another aspect, "moderate expression" of PCBP-1 can be between a 2- to 3-fold increase in PCBP-1 expression as compared to normal tissues. In another aspect, "weak expression" of PCBP-1 can be a 1-fold or less increase in PCBP-1 expression as compared to normal tissues. In another aspect, "weak expression" of PCBP-1 can be a decrease in PCBP-1 expression as compared to normal tissues.

In another aspect of the present invention, increases in PCBP-1 expression can be expressed as increases in cells or tissues as a whole. In another aspect, increases in PCBP-1 expression can be expressed as increases in the cytoplasm of cells. In another aspect, increases in PCBP-1 expression can be expressed as increases in the nucleus of cells.

In another aspect of the present invention, decreases in PCBP-1 expression can be expressed as decreases in cells or tissues as a whole. In another aspect, decreases in PCBP-1 expression can be expressed as decreases in the cytoplasm of cells. In another aspect, decreases in PCBP-1 depression can be expressed as increases in the nucleus of cells.

In one aspect of the present invention, PCBP-1 expression in colon cancer cells is increased as compared to PCBP-1 expression in normal colon cells. In another aspect, colon cancer cells can exhibit strong cytoplasmic PCBP-1 expression as compared to normal colon cells.

In one aspect of the present invention, PCBP-1 expression in squamous carcinoma cells is increased as compared to PCBP-1 expression in normal skin cells. In another aspect, squamous carcinoma cells can exhibit a greater than 3-fold increase cytoplasmic PCBP-1 expression as compared to normal skin cells.

In another aspect of the present invention, PCBP-1 expression in melanoma cells is increased as compared to PCBP-1 expression in normal skin cells. In another aspect, melanoma cells can exhibit strong cytoplasmic PCBP-1 expression, while normal skin cells can exhibit weak nuclear expression of PCBP-1.

In one aspect of the present invention, PCBP-1 expression in glioblastoma multiforme cells is increased as compared to PCBP-1 expression in normal brain cells. In another aspect, glioblastoma multiforme cells can exhibit moderate cytoplasmic expression of PCBP-1, while neurons and astrocytes do not exhibit any PCBP-1 expression.

In one aspect of the present invention, PCBP-1 expression in astrocytoma cells is increased as compared to PCBP-1 expression in normal brain cells. In another aspect, astrocytoma cells can exhibit moderate cytoplasmic expression of PCBP-1, while neurons and astrocytes do not exhibit any PCBP-1 expression.

In one aspect of the present invention, PCBP-1 expression in ovarian cancer cells is decreased as compared to PCBP-1 expression in normal skin cells. In another aspect, ovarian cancer cells can exhibit little or no nuclear and/or cytoplasmic expression of PCBP-1, while normal ovarian cells can exhibit strong nuclear and cytoplasmic expression of PCBP-1.

In one aspect of the present invention, PCBP-1 expression in endometrial cancer cells is increased as compared to PCBP-1 expression in normal endometrial cells. In another aspect, endometrial cancer cells can exhibit strong nuclear and cytoplasmic PCBP-1 expression, while normal endometrial cells can exhibit little or no cytoplasmic expression of PCBP-1.

In one aspect of the present invention, PCBP-1 expression in sarcoma cells is increased as compared to PCBP-1 expression in normal muscle cells. In another aspect, sarcoma cells can exhibit moderate to high levels of cytoplasmic PCBP-1 expression as compared to normal muscle cells.

In one aspect of the present invention, PCBP-1 expression in bladder cancer cells is increased as compared to PCBP-1 expression in normal bladder cells. In another aspect, bladder cancer cells can exhibit moderate to high levels of cytoplasmic PCBP-1 expression as compared to normal bladder cells.

In one aspect of the present invention, PCBP-1 expression in breast cancer cells can be increased as compared to PCBP-1 expression in normal breast cells. In another aspect, breast cancer cells can exhibit strong cytoplasmic PCBP-1 expression and moderately strong nuclear PCBP-1 expression, while normal breast cells can exhibit weak nuclear PCBP-1 expression. In another aspect, breast cancer cells can exhibit strong cytoplasmic PCBP-1 expression and moderately strong nuclear PCBP-1 expression, while normal breast cells can exhibit strong nuclear PCBP-1 expression.

In an aspect of the present invention a similar level of a soluble form of PCBP-1 in a cell, collection of cells or sample to a normal control can diagnose, prognose, monitor, determine, confirm or indicate that such cell was derived from a non-metastatic tissue.

In an aspect of the present invention, a lack of localization of a soluble form of PCPB-1 in a cell nucleus can diagnose, prognose, monitor, determine, confirm or indicate that such derived is from a metastatic tissue In an aspect of the present invention, localization of a soluble form of PCPB-1 in a cell, collection of cells or sample to a normal control can diagnose, prognose, monitor, determine, confirm or indicate that such derived from a non-metastatic tissue.

In an aspect of the present invention, the cell, collection of cells or sample is a cervical or breast cell collection of cells or sample.

Antibodies and antibody fragments of the present invention are also useful for immunopathological analysis, such as the differential diagnosis of tumor type, and the subclassification of the tumor based on its expression of PCBP-1, including, without limitation, assessment of metastatic potential, predicted responses to therapy, and overall prognosis.

PCBP-1 antibodies and antibody fragments permit the definition of subpopulations of tumor cells among the heterogeneous cells present in a growing tumor and can be used, for example, in the typing and cross-matching of the tumor cell "lines," including, without limitation, by means of flow cytometry, both at the time of surgery and prior to therapy. An analysis of the tumor cell populations or subpopulations with antibodies or antibody fragments of this invention, and a battery of additional antibodies or antibody fragments, can be used to define (a) which antigen preparation would be the most appropriate for specific active immunotherapy, (b) which antibody or antibody fragment or chimeric antibody would be efficacious for the particular cancer; and (c) which antibody or combination of antibodies or antibody fragments should be used for imaging the patient at a later date in search for recurrent or metastatic tumors.

A biological sample can be treated with nitrocellulose, or other solid support or carrier which is capable of immobilizing cells, cell particles or soluble proteins or glycoproteins. The support can then be washed with suitable buffers followed by treatment with the detectably labeled antibody of the present invention. The solid phase support can then be washed with the buffer a second time to remove unbound antibody. The amount of bound label on said solid support can then be detected by conventional means.

One of the ways in which the antibody of the present invention can be detectably labeled is by linking the same to an enzyme and use in an enzyme immunoassay (EIA) or enzyme-linked immunosorbent assay (ELISA). This enzyme, when subsequently exposed to its substrate, will react with the substrate generating a chemical moiety which can be detected, for example, by spectrophotometric, fluorometric or by visual means. In an alternate embodiment, the enzyme is used to label a binding partner for the antibody of the invention. Such a binding partner can be an antibody against the constant or variable region of the antibody of the invention, such as a heterologous anti-mouse immunoglobulin antibody. Alternatively, the binding partner can be a non-antibody protein capable of binding to the antibody of the present invention.

By radioactively labeling the antibodies of the present invention, it is possible to detect PCBP-1 through the use of a radioimmunoassay (RIA). The radioactive isotope can be detected by such means as the use of a gamma counter or a scintillation counter or by autoradiography. Isotopes which are particularly useful for the purpose of the present invention are known in the art.

It is also possible to label the antibodies of the present invention with a fluorescent compound. When the fluorescently labeled antibody is exposed to light of the proper wave length, its presence can then be detected due to fluorescence. The antibodies of the present invention also can be detectably labeled by coupling to a chemiluminescent compound. The presence of the chemiluminescently labeled antibody is then determined by detecting the presence of luminescence that arises during the course of a chemical reaction. A bioluminescent compound can also be used to label the antibodies of the present invention. Bioluminescence is a type of chemiluminescence found in biological systems, in which a catalytic protein increases the efficiency of the chemiluminescent reaction. The presence of a bioluminescent protein is determined by detecting the presence of luminescence. Important bioluminescent compounds for purposes of labeling are luciferin, luciferase and sequorin.

Detection of the antibody, fragment or derivative can be accomplished by a scintillation counter, for example, if the detectable label is a radioactive gamma emitter, or by a fluorometer, for example, if the label is a fluorescent material. In the case of an enzyme label, the detection can be accomplished by colorimetric methods which employ a substrate for the enzyme. Detection can also be accomplished by visual comparison of the extent of enzymatic reaction of a substrate in comparison with similarly prepared standards.

In situ detection can be accomplished by removing a specimen from a patient, and providing the labeled antibody, or the unlabelled antibody plus a labeled binding partner to such a specimen. Through the use of such a procedure, it is possible to determine not only the presence of the antigen but also its distribution in the examined tissue. Using the present invention, those of ordinary skill will readily perceive that any of a wide variety of histological methods (such as staining procedures) can be modified in order to achieve such in situ detection. Such methods include, for example, immunohistochemical staining procedures. In an aspect, an avidin-biotin immunoperoxidase staining system can be used, and a kit utilizing this system is also contemplated, although the methods of the present invention can utilize any suitable staining procedures known in the art.

Kits according to the present invention can include frozen or lyophilized antibodies to be reconstituted by thawing or by suspension in a liquid vehicle. The kits can also include a carrier or buffer. Preferably, the kit also comprises instructions for reconstituting and using the antibody. The kit employing antibodies, including chimeric and humanized antibodies of the present invention, can be used for immunohistochemical evaluation of cancers, including cancer of the breast, ovary, cervix, prostate, colon, stomach, kidney, liver, head, neck, lung, blood, pancreas, skin, testicle, thyroid and brain.

The kits including the reagents necessary for immunohistochemical analysis can be provided as follows: a) PCBP-1 antibody or antibody fragment of the present invention, or chimeric or humanized variants thereof; b) blocking reagent (in the form of, for example, goat serum) and secondary antibody (such as, for example, goat anti-mouse antibody); c) detectable marker (such as, for example, immunoperoxidase or alkaline phosphatase); and d) developing reagents. The primary antibody (PCBP-1 antibody or antibody fragment or variants thereof) serves as an antigen which can bind more than one secondary antibody. The secondary antibodies form a "bridge" between the primary antibody and the complex formed by the detectable marker and developing reagent (for example, a horseradish peroxidase-antiperoxidase complex).

Any suitable detection system can be used in accordance with the methods and kits of the present invention. Such detection systems are widely used in immunofluorescence applications, and can be imaged using techniques including, but not limited to, flow cytometry, microscopy, Western blotting, and ELISAs. Suitable detection systems can employ conjugates of secondary antibodies, conjugates of colloidal gold, or conjugates of secondary proteins, in order to amplify the signal from a primary protein (in the context of the present invention, the primary protein signal being amplified is bound a PCBP-1 antibody, which can or cannot be labeled, for example with a protein such as biotin), which is in turn being used to detect a specific target (in the context of the present invention, the target is a PCBP-1 expression product).

Suitable secondary conjugates for use in the methods and kits of the present invention can include, but are not limited to, enzyme conjugates of a secondary antibody and an enzyme such as horseradish peroxidase or alkaline phosphatase; enzyme conjugates of avidin or streptavidin and an enzyme such as horseradish peroxidase or alkaline phosphatase; enzyme conjugates of protein A or protein G and an enzyme such as horseradish peroxidase or alkaline phosphatase; conjugates of colloidal gold and a secondary antibody; conjugates of colloidal gold and avidin or streptavidin; conjugates of magnetic particles and a secondary antibody; and conjugates of secondary antibodies and labels such as fluorescent dyes and biotin. The present invention is not limited to any particular detection systems, and it is considered within the ability of the person of ordinary skill in the art to utilize these or other detection systems in accordance with the present invention. These secondary conjugates (also referred to as labels in the context of the present invention) are useful for visualizing antigen-antibody complexes.

The antibody or antibody fragment of the present invention can also be adapted for utilization in an immunometric assay, also known as a "two-site" or "sandwich" assay. In a typical immunometric assay, a quantity of unlabelled antibody (or fragment of antibody), is bound to a solid support that is insoluble in the fluid being tested and a quantity of detectably labeled soluble antibody is added to permit detection and/or quantitation of the ternary complex formed between solid-phase antibody, antigen, and labeled antibody.

For purposes of in vivo imaging of colon, breast, ovarian and other cancers using the antibodies or antibody fragments of the present invention, there are many different labels and methods of labeling known to those of ordinary skill in the art. Examples of the types of labels which can be used in the present invention include radioactive isotopes, paramagnetic isotopes, and compounds which can be imaged by positron emission tomography (PET).

6. Pharmaceutical Compositions and Methods of Treatment

Another aspect of the invention provides a composition comprising any of these antibodies, optionally in combination with a pharmaceutically acceptable carrier. In another aspect, an antibody of the present invention is optionally in combination with one or more active agents, drugs or hormones.

The present invention also provides a method of treating human or animal subjects suffering from or at risk of a cancer that expresses PBCP-1, such as solid tumors of the breast, ovary, cervix, prostate, colon, stomach, kidney, liver, head, neck, lung, pancreas, skin, testicle, thyroid and brain, the method comprising administering to the subject a therapeutically effective amount of an antibody of the present invention, or a pharmaceutical composition comprising a therapeutically effective amount of an antibody of the present invention.

The term "subject" as used herein refers to any subject in need of treatment.

The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective dose can be estimated initially either in cell culture assays or in animal models, usually in rodents, rabbits, dogs, pigs, or primates. The animal model can also be used to determine the appropriate concentration range and route of administration. Such information can then be used to determine useful doses and routes for administration in humans.

An effective amount for a human subject can depend upon the severity of the disease state, the general health of the subject, the age, weight and gender of the subject, diet, time and frequency of administration, drug combination(s), reaction sensitivities and tolerance/response to therapy and can be determined by routine experimentation and is within the judgment of the clinician. Generally, an effective dose will be from 0.01 mg/kg to 50 mg/kg, preferably 0.1 mg/kg to 20 mg/kg, more preferably from about 1 mg/kg to about 15 mg/kg.

Compositions can be administered individually to a patient or can be administered in combination with other agents, drugs or hormones. According to some aspects, antibodies can be conjugated with these agents. A summary of the ways in which the antibodies of the present invention can be used therapeutically includes direct cytotoxicity by the antibody, either mediated by complement or by effector cells, or conjugated to anti-tumor drugs, toxins, and radionuclides. Antibodies can also be used for ex vivo removal of tumor cells from the circulation or from bone marrow.

Cytotoxic proteins can include, but are not limited to, Ricin-A, *Pseudomonas* toxin, Diphtheria toxin, and tumor necrosis factor. Diagnostic radionuclides and cytotoxic agents such as cytotoxic radionuclides, drug and proteins can also be conjugated to the antibodies of the present invention. Examples of radionuclides which can be coupled to antibodies and selectively delivered in vivo to sites of antigen include $^{212}$Bi, $^{131}$I, $^{186}$Re, and $^{90}$Y, among others. Radionuclides can exert their cytotoxic effect by locally irradiating the cells, leading to various intracellular lesions, as is known in the art of radiotherapy. Examples of cytotoxic drugs which can be conjugated to antibodies and subsequently used for in vivo therapy include, but are not limited to, daunorubicin, doxorubicin, methotrexate, and Mitomycin C. Cytotoxic drugs can interface with critical cellular processes including DNA, RNA, and protein synthesis.

A dose at which the antibody molecule of the present invention is administered depends on the nature of the condition to be treated, and on whether the antibody molecule is being used prophylactically or to treat an existing condition. If administered prophylactically, i.e., as a vaccine, the antibody is administered in an amount effective to elicit an immune response in the subject.

If the antibody molecule has a short half-life (e.g. 2 to 10 hours) it can be necessary to give one or more doses per day. Alternatively, if the antibody molecule has a long half life (e.g. 2 to 15 days) it can only be necessary to give a dosage once per day, per week or even once every 1 or 2 months.

A pharmaceutical composition can also contain a pharmaceutically acceptable carrier for administration of the antibody. The carrier should not itself induce the production of antibodies harmful to the individual receiving the composition and should not be toxic. Suitable carriers include those known in the art, and can be selected from large, slowly metabolized macromolecules such as proteins, polypeptides, liposomes, polysaccharides, polylactic acids, polyglycolic acids, polymeric amino acids, amino acid copolymers and inactive virus particles, although suitable carriers are not limited to these examples.

Preferred forms for administration include forms suitable for parenteral administration, e.g. by injection or infusion, for example by bolus injection or continuous infusion. Where the product is for injection or infusion, it can take the form of a suspension, solution or emulsion in an oily or aqueous vehicle and it can contain formulatory agents, such as suspending, preservative, stabilizing and/or dispersing agents. Alternatively, the antibody molecule can be in dry form, for reconstitution before use with an appropriate sterile liquid.

Once formulated, the compositions of the invention can be administered directly to the subject. The subjects to be treated can be animals. However, it is preferred that the compositions are adapted for administration to human subjects.

A pharmaceutical compositions of this invention can be administered by any number of routes including, but not limited to, oral, intravenous, intramuscular, intra-arterial, intramedullary, intrathecal, intraventricular, transdermal, transcutaneous, subcutaneous, intraperitoneal, intranasal, enteral, topical, sublingual, intravaginal or rectal routes. Hyposprays can also be used to administer the pharmaceutical compositions of the invention. Therapeutic compositions can be prepared as injectables, either as liquid solutions or suspensions. Solid forms suitable for solution in, or suspension in, liquid vehicles prior to injection can also be prepared.

Direct delivery of the compositions will generally be accomplished by injection, subcutaneously, intraperitoneally, intravenously or intramuscularly, or delivered to the interstitial space of a tissue. Dosage treatment can be a single dose schedule or a multiple dose schedule.

When an antibody or antibody fragment composition is to be administered by a route using the gastrointestinal tract, the composition can to contain additional agents which protect the antibody from degradation but which release the antibody once it has been absorbed from the gastrointestinal tract. Such additional agents are well-known to those skilled in the art.

Antibodies of the present invention can also be administered in methods of conducting gene therapy. In order to achieve this, DNA sequences encoding the heavy and light chains of the antibody molecule under the control of appropriate DNA components are introduced into a patient such that the antibody chains are expressed from the DNA sequences and assembled in situ.

7. PCBP-1 Expression Products as Drug Development Targets

In addition, the present invention relates to the discovery that Pcbp-1 and homologues thereof can cause the expression of PCBP-1 antigens by cells in patients suffering from various diseases, such as cancers, and more specifically solid tumors of the breast, ovary, cervix, prostate, colon, stomach, kidney, liver, head, neck, lung, pancreas, skin, testicle, thyroid and brain. This expression of PCBP-1 antigens presents a drug development target, and accordingly the present invention also relates to the use of such PCBP-1 antigens as biomarkers that can be targeted not only by the PCBP-1 antibodies or antibody fragments of the present invention, but also by various other molecules, such as siRNA, antisense oligonucleotides, vaccines, and chemical compounds.

Methods for developing drugs useful in treating and/or diagnosing diseases characterized by the expression of gene products of Pcbp-1 and homologues thereof can include the steps of identifying the gene products expressed by Pcbp-1 and homologues thereof in a subject having a disease, and utilizing those gene products as to development and identify drugs that specifically target the gene products.

Once candidate drugs have been developed based on the PCBP-1 antigens, the PCBP-1 antigens and PCBP-1 antibodies and antibody fragments of the present invention can be used to aid in screening the various drug candidates, in order to identify those drug candidates that exhibit a desired level of specificity for diseased cells presenting PCBP-1 expression products.

The following examples are non-limiting illustrative examples.

EXAMPLE 1

Before tumor resection, 10 ml samples of blood are collected from ovarian or breast cancer patients into EDTA-containing tubes and placed on ice immediately. Within two hours of collection, blood samples are centrifuged at 1000×g for 20 minutes. The buffy coat and red blood cell layers are removed and the plasma is stored as 250-500 µl aliquots at −70° C. until analysis. Patients with stage II, III, and IV ovarian or breast cancers are selected for this study. Controls are obtained from healthy, cancer-free women who donated blood to the Brigham and Women's Hospital Blood Bank. Blood from breast cancer patients is collected in sodium citrate tubes (Becton-Dickinson) and processed according to the manufacturer's instructions. Plasma samples are aliquoted and stored at −80° C. until analyzed.

Plasma samples isolated from 20 patients with stage II-IV ovarian cancer are obtained from Brigham and Women's Hospital. Plasma samples (C: control breast blood sample, NM: non-metastatic breast blood sample, M: metastatic breast blood sample) obtained from control and patient groups are diluted with PBS at a ratio of 1:100. An increase in soluble plasma filamin-A levels have been reported to be associated with cancer. Plasma filamin-A levels are measured with an enzyme-linked immunosorbent enzyme assay. The ELISA plates (Nalge NUNC International, Rochester, N.Y.) are coated with 100 µl/well of diluted plasma and incubated at 4° C. overnight. The blood plasma samples are analyzed in a blinded fashion. The wells are washed with PBS and incubated at room temperature for one hour with blocking buffer (5% BSA in PBS). After washing with PBS, the primary antibody, A-FLNA is added in dilution buffer (45 µg/ml) (PBS buffer, 1% BSA, 0.01% Tween-20). The wells are washed with PBS/0.03% Tween-20 and incubated at room temperature for one hour with 100 µl/well secondary antibody (HRP-Donkey anti-mouse IgG, Jackson ImmunoResearch, West Grove, Pa.) diluted 1:3000. After washing the wells, 100 µl Immunopure TMB substrate solution (Pierce, Rockford, Ill.) is added. Color reaction is stopped by the addition of 100 µl/well 1N $H_2SO_4$ and the analysis is performed with an ELISA Reader. The figures represent optical density (OD) values of plasma readings for filamin-A levels. P-values are derived using the Mann Whitney Test and show a significant difference among control, non-metastatic and metastatic groups (p<0.001). P values are determined by comparison with controls by ANOVA. Data are representative of four independent experiments performed in triplicate. All analyses are performed under blinded conditions. See FIG. 1.

Figure 2A:
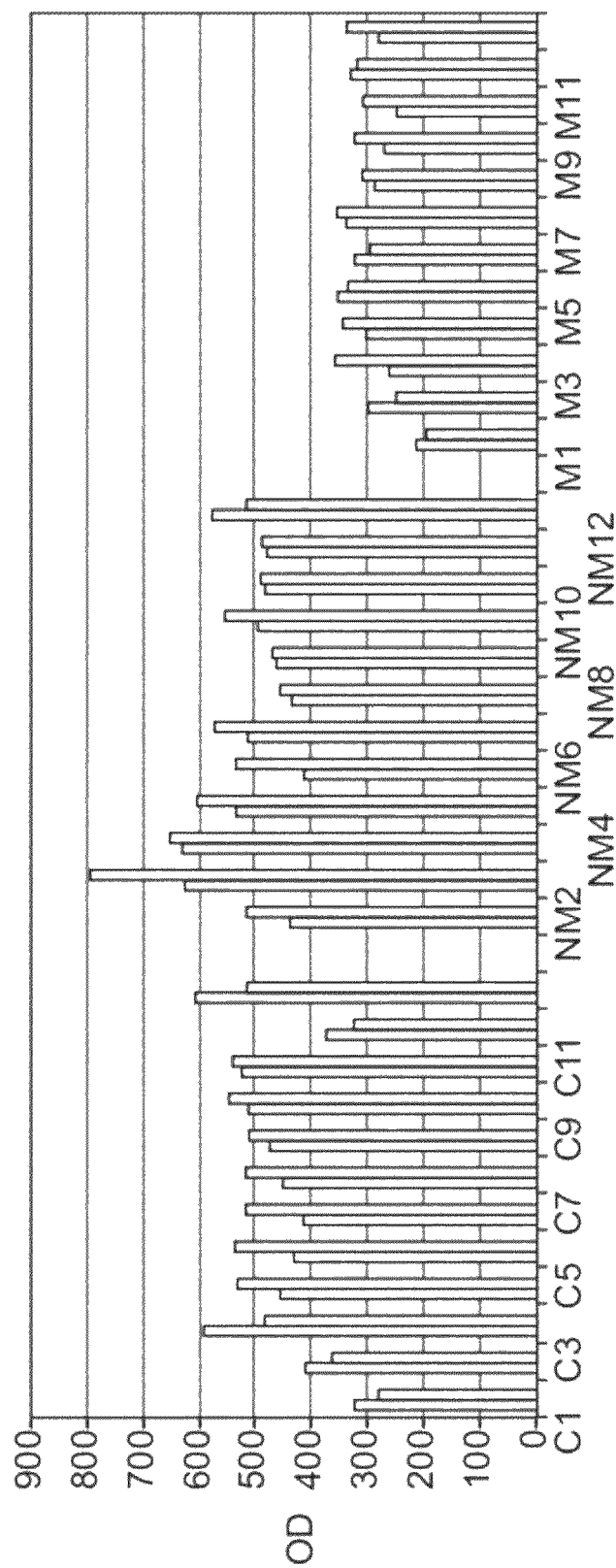
FIG. 2A is a bar graph of duplicate ELISA results.
Figure 2B:
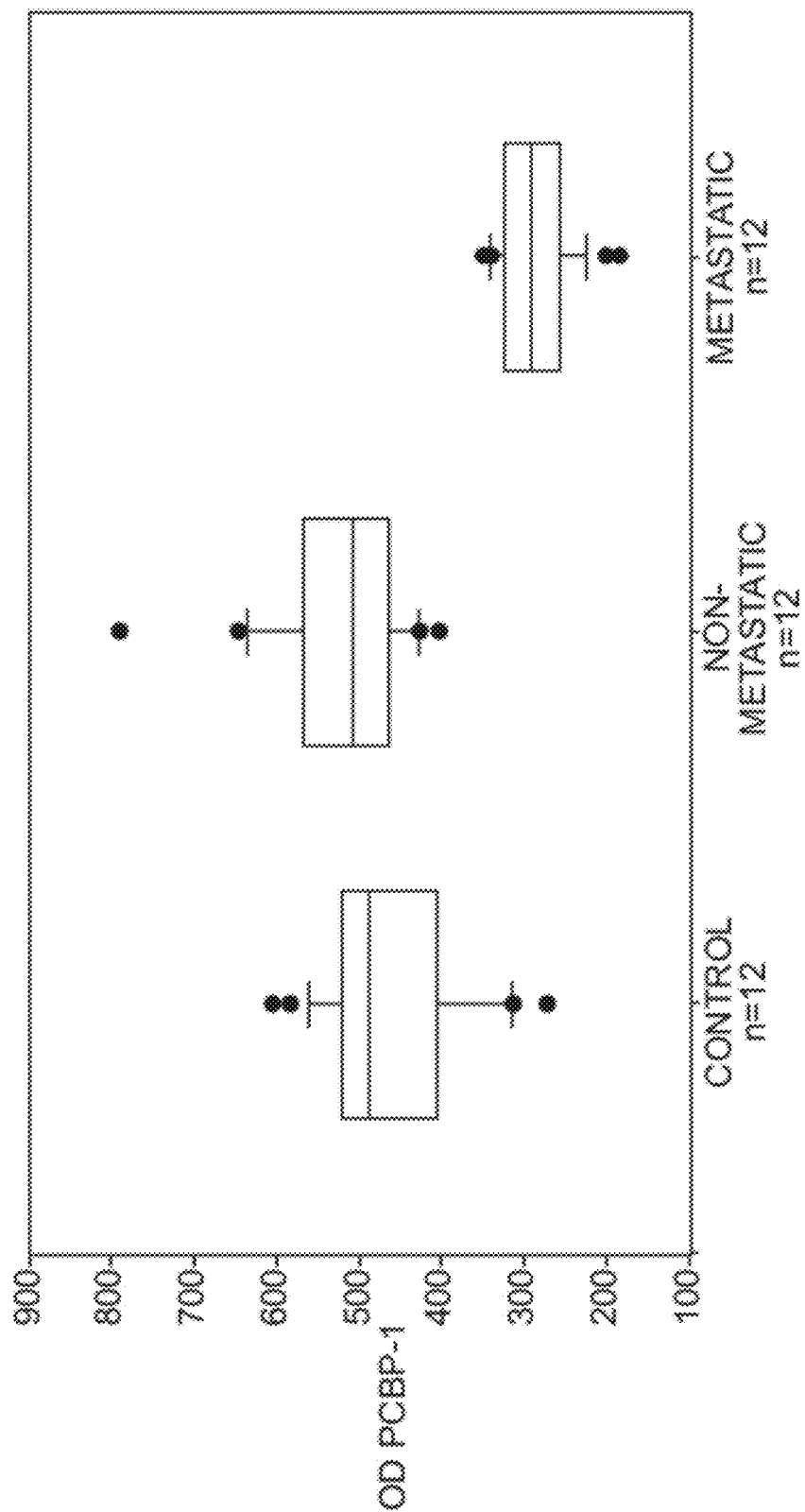
FIG. 2B is a box plot of averaged ELISA results.

Plasma samples from breast cancer patients are subjected to ELISA analysis using the anti-PCBP-1 monoclonal antibody. Plasma samples (C: control breast blood sample, NM: non-metastatic breast blood sample, M: metastatic breast blood sample) obtained from control and patient groups are diluted with PBS at a ratio of 1:100. Plasma PCBP-1 levels are measured with an enzyme-linked immunosorbent enzyme assay. The ELISA plates (Nalge NUNC International, Rochester, N.Y.) are coated with 100 µl/well of diluted plasma and incubated at 4° C. overnight. The blood plasma samples are analyzed in a blinded fashion. The wells are washed with PBS and incubated at room temperature for one hour with blocking buffer (5% BSA in PBS). After washing with PBS, the primary antibody, anti-PCBP-1 is added in dilution buffer (45 µg/ml) (PBS buffer, 1% BSA, 0.01% Tween-20). The wells are washed with PBS/0.03% Tween-20 and incubated at room temperature for one hour with 100 µl/well secondary antibody (HRP-Donkey anti-mouse IgG, Jackson ImmunoResearch, West Grove, Pa.) diluted 1:3000. After washing the wells, 100 µl Immunopure TMB substrate solution (Pierce, Rockford, Ill.) is added. Color reaction is stopped by the addition of 100 µl/well 1N $H_2SO_4$ and the analysis is performed with an ELISA Reader. The figures represent optical density (OD) values of plasma readings for PCBP-1 levels. P-values are derived using the Mann Whitney Test. Control and metastatic group showed a significant difference (p<0.001). Control and non-metastatic groups did not show a significant difference. There is a significant difference between non-metastatic and metastatic groups (p<0.001). P values are determined by comparison with controls by ANOVA. Data are representative of four independent experiments performed in triplicate. All analyses are performed under blinded conditions. See FIGS. 2A and 2B.

EXAMPLE 2

Cellular Localization of PCBP-1 in Human Breast Cancer Cells

Figure 3:
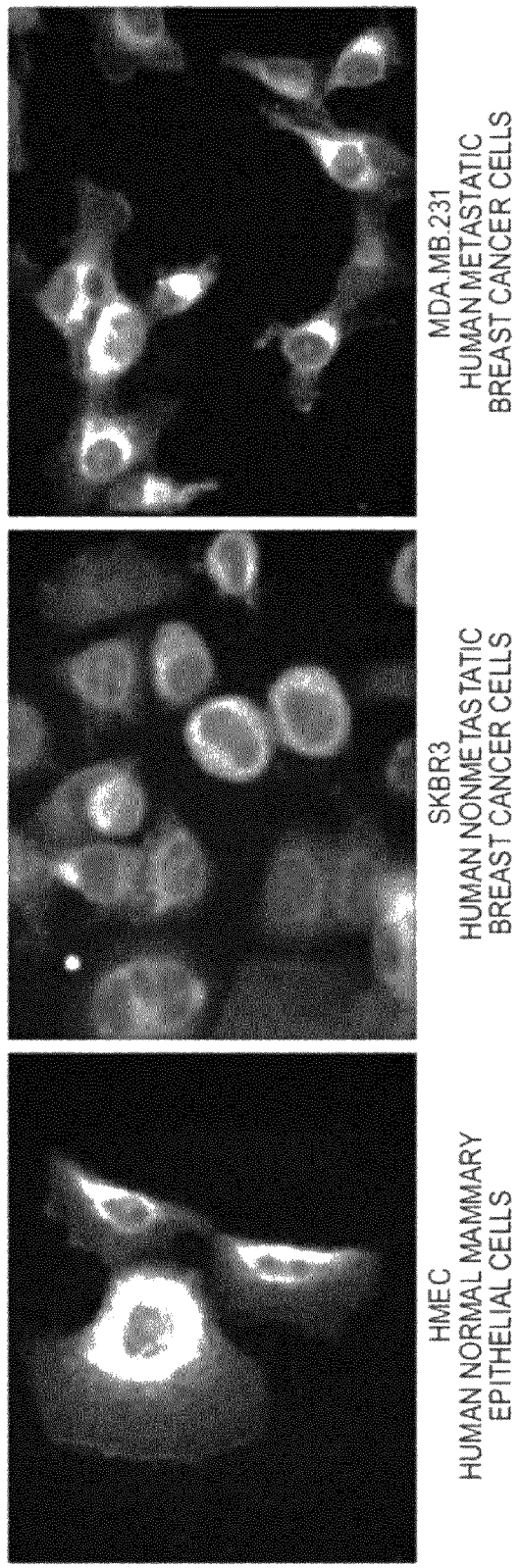
FIG. 3. Human normal mammary epithelial cells (HMECs), SKBR3 cells (human non-metastatic breast cancer cells) and MDA-MB-231 cells (human metastatic breast cancer cells) are seeded and grown on glass slides. The cells are fixed with formalin (10% with 0.1% Triton-X), washed with PBB and stained with anti-PCBP-1 mouse monoclonal antibody. Cells are then labeled with a FITC-labeled secondary goat-anti-mouse antibody and subjected to laser confocal microscopy. Indirect immunofluorescent staining is observed in the cytoplasm of HMECs. SKBR3 cells exhibit cytoplasmic and nuclear staining MDA-MB-231 cells exhibit cytoplasmic staining.

Human normal mammary epithelial cells (HMECs), SKBR3 cells (human non-metastatic breast cancer cells) and MDA-MB-231 cells (human metastatic breast cancer cells) are seeded and grown on glass slides. The cells are fixed with formalin (10% with 0.1% Triton-X), washed with PBS and stained with anti-PCBP-1 mouse monoclonal antibody. Cells are then labeled with a FITC-labeled secondary goat-anti-mouse antibody and subjected to laser confocal microscopy. Indirect immunofluorescent staining is observed in the cytoplasm of HMECs. SKBR3 cells exhibit cytoplasmic and nuclear staining MDA-MB-231 cells exhibit cytoplasmic staining See FIG. 3.

EXAMPLE 3

Cellular Localization of PCBP-1 in Human Cervical Cells

Cervical cells obtained from pap smears of healthy and cervical cancer patients are seeded and grown on glass slides. The cells are fixed with formalin (10% with 0.1% Triton-X), washed with PBS and stained with anti-PCBP-1 mouse monoclonal antibody. Cells are then labeled with a FITC-labeled secondary goat-anti-mouse antibody and subjected to laser confocal microscopy. Indirect immunofluorescent staining is observed in the cytoplasm and nucleus of normal cervical cells. Cervical cancer cells (CIN III) display cytoplasmic staining only. See FIG. 4.

EXAMPLE 4

Figure 5:
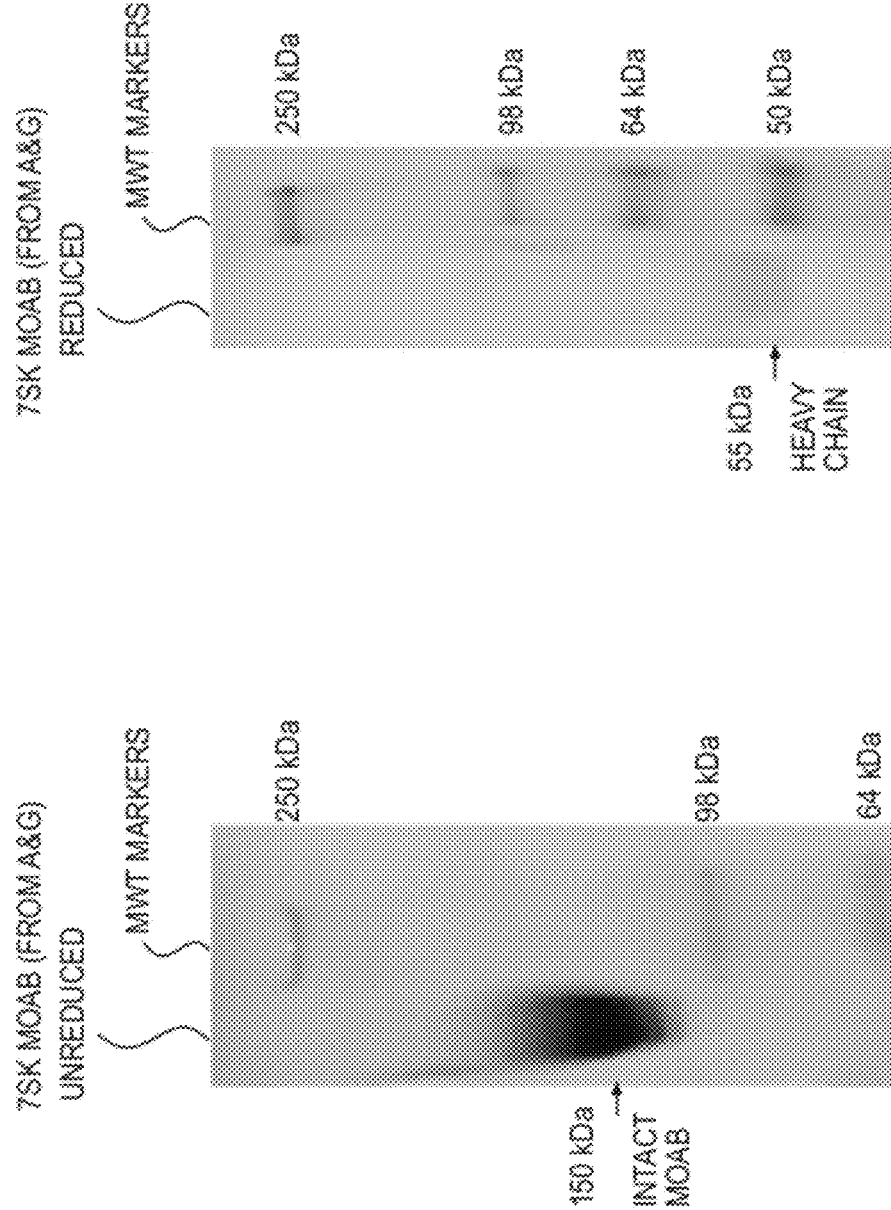
FIG. 5. Approximately 2 μg of purified Alper PCBP-1 mouse mAb (identified as 7SK) is suspended in PBS, and is applied under reducing (boiled 3 minutes in sample buffer with beta-merkaptoethanol and 10% SDS) and non-reducing (not boiled, and without beta-merkaptoethanol) conditions to 6 and 8% Tris-glycine gels and run at 120 volts. The gels are then stained with Coomassie Blue (0.1% (w/v) Coomassie blue R350, 20% (v/v) methanol, and 10% (v/v) acetic acid), destained in 50% (v/v) methanol in water with 10% (v/v) acetic acid, and images of the gels are taken. Molecular weight markers are shown on the right. The 6% Tris-glycine gel shows the Alper PCBP-1 mouse IgG1 antibody (7SK) at ~150 kDa under non-reduced conditions. The 8% Tris-glycine gel shows the heavy chain of the Alper PCBP-1 mouse IgG1 antibody (7SK) at ~50 kDa.

Approximately 2 µg of a purified 7SK mAb is suspended in PBS, and is applied under reducing (boiled 3 minutes in sample buffer with beta-mercaptoethanol and 10% SDS) and non-reducing (not boiled, and without beta-mercaptoethanol) conditions to 6 and 8% Tris-glycine gels and run at 120 volts. The gels are then stained with Coomassie Blue (0.1% (w/v) Coomassie blue R350, 20% (v/v) methanol, and 10% (v/v) acetic acid), destained in 50% (v/v) methanol in water with 10% (v/v) acetic acid, and images of the gels are taken. Molecular weight markers are shown on the right. The 6% Tris-glycine gel shows the IgG1 antibody (7SK) at ~150 kDa under non-reduced conditions. The 8% Tris-glycine gel shows the heavy chain of the IgG1 antibody (7SK) at ~50 kDa. See FIG. 5.

EXAMPLE 5

Figure 6:
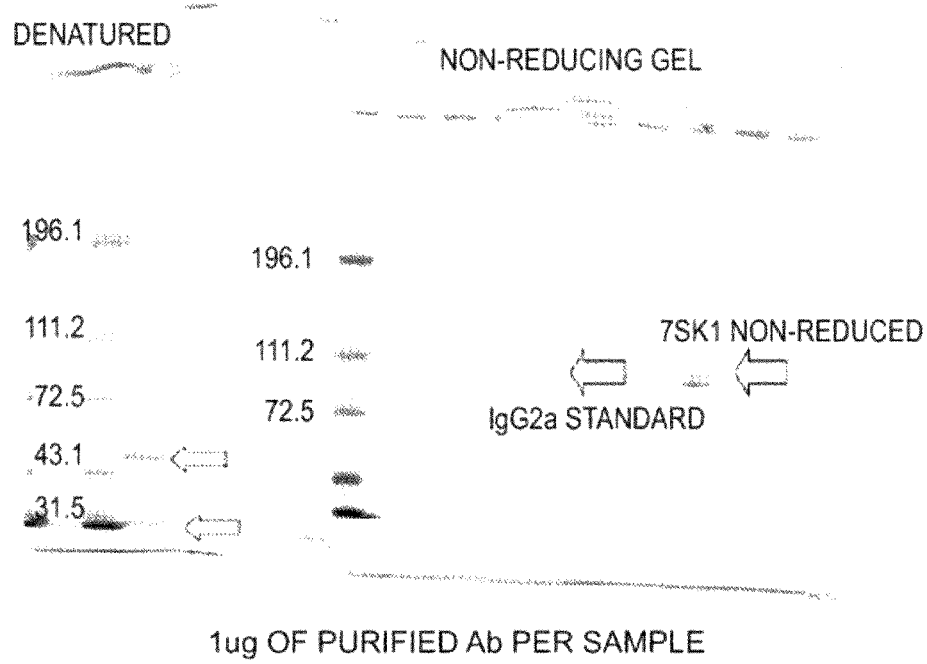
FIG. 6. Approximately 1 μg of purified Alper PCBP-1 mouse mAb (identified as 7SK) is suspended in PBS, and is applied under reducing (boiled 3 minutes in sample buffer with beta-merkaptoethanol and 10% SDS) and non-reducing (not boiled, and without beta-merkaptoethanol) conditions to 8% Tris-glycine gels and run at 120 volts. The gels are then stained with Coomassie Blue (0.1% (w/v) Coomassie blue R350, 20% (v/v) methanol, and 10% (v/v) acetic acid), destained in 50% (v/v) methanol in water with 10% (v/v) acetic acid, and images of the gels are taken. Molecular weight markers are shown on the left. Under denatured conditions, the heavy chain of Alper PCBP-1 mouse IgG1 Ab (7SK) is detected at ~50 kDa and light chain of Alper PCBP-1 mouse IgG1 (7SK) is detected at ~25 kDa. In a non-reducing gel, intact Alper PCBP-1 mouse IgG1 (7SK) is detected at 150 kDa.

Approximately 1 µg of a purified 7SK mAb is suspended in PBS, and is applied under reducing (boiled 3 minutes in sample buffer with beta-mercaptoethanol and 10% SDS) and non-reducing (not boiled, and without beta-mercaptoethanol) conditions to 8% Tris-glycine gels and run at 120 volts. The gels are then stained with Coomassie Blue (0.1% (w/v) Coomassie blue R350, 20% (v/v) methanol, and 10% (v/v) acetic acid), destained in 50% (v/v) methanol in water with 10% (v/v) acetic acid, and images of the gels are taken. Molecular weight markers are shown on the left. Under denatured conditions, the heavy chain of IgG1 Ab (7SK) is detected at ~50 kDa and light chain of IgG1 (7SK) is detected at ~25 kDa. In a non-reducing gel, intact IgG1 (7SK) is detected at 150 kDa. See FIG. 6.

EXAMPLE 6

Figure 7:
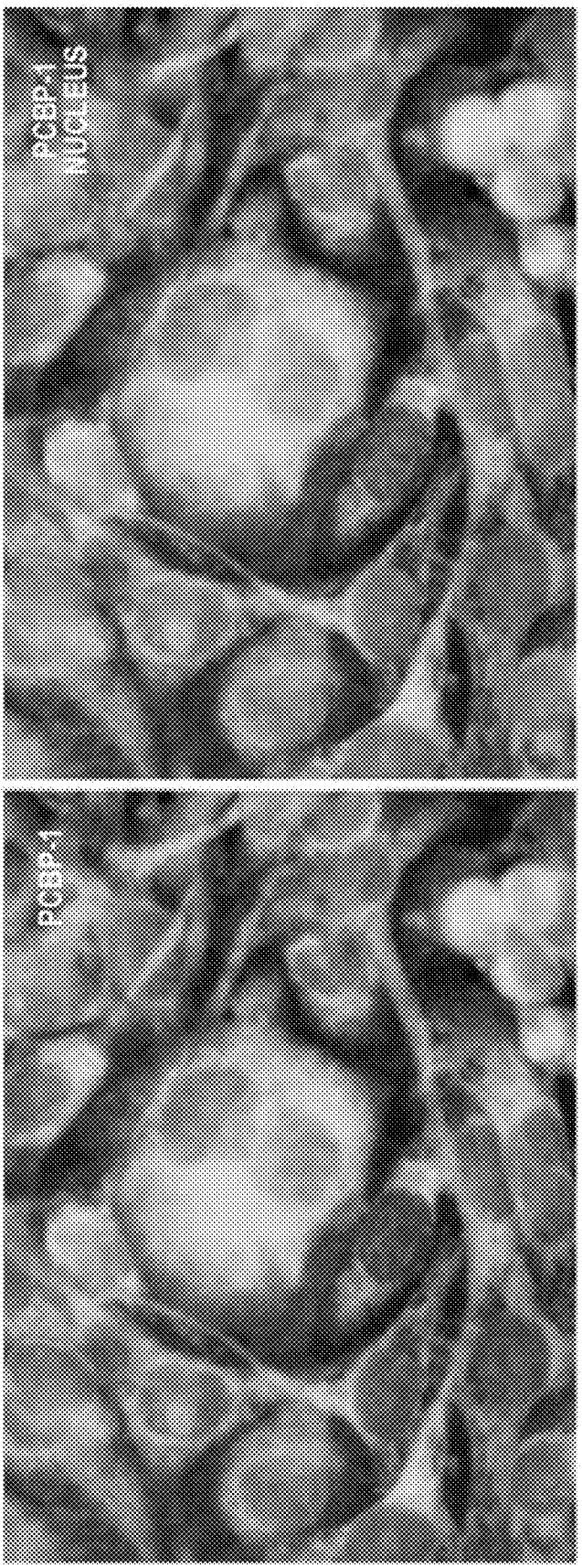
FIG. 7. SKBR3 cells are fixed with 10% gluteraldehyde, permeabilized with 0.1% Triton-X100. PCBP-1 expression is then visualized with the Alper PCBP-1 mouse mAb (7SK) and secondary FITC-labeled anti-mouse antibodies (Jackson ImmunoResearch, West Grove, Pa.). Nuclei are visualized by DAPI staining (Molecular Probes, Eugene, Oreg.). The images are analyzed using a Olympus microscope equipped with 63× objective lens.

SKBR3 cells are fixed with 10% gluteraldehyde, permeabilized with 0.1% Triton-X100. PCBP-1 expression is then visualized with the 7SK mAb and secondary FITC-labeled anti-mouse antibodies (Jackson ImmunoResearch, West Grove, Pa.). Nuclei are visualized by DAPI staining (Molecular Probes, Eugene, Oreg.). The images are analyzed using a Olympus microscope equipped with 63× objective lens. See FIG. 7.

EXAMPLE 7

Spot 1 is digested with trypsin and analyzed by MALDI-MS. The major protein identified is poly(rC)-binding protein 1, SwissProt Q15365. Also present, probably as contaminants, are albumin (fragment) and hemoglobin alpha and beta.

EXAMPLE 8

Figure 8:
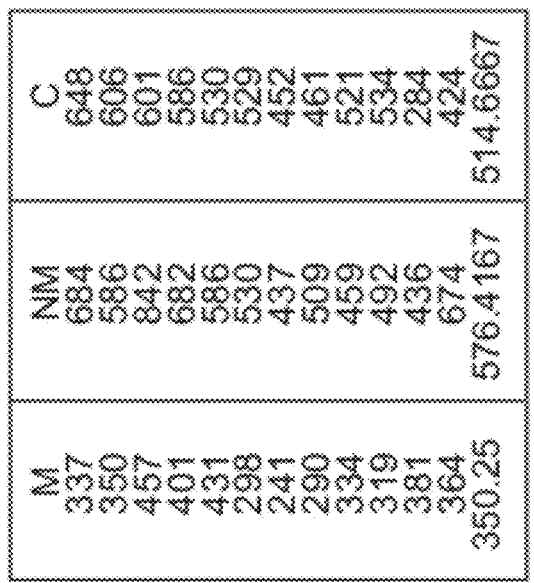
FIG. 8. Plasma samples (C: control breast blood sample, NM: non-metastatic breast blood sample, M: metastatic breast blood sample) obtained from control and patient groups are diluted with PBS at a ratio of 1:100. Plasma PCBP-1 levels are measured with an enzyme-linked immunosorbent enzyme assay. The ELISA plates (Nalge NUNC International, Rochester, N.Y.) are coated with 100 µl/well of diluted plasma and incubated at 4° C. overnight. The blood plasma samples are analyzed in a blinded fashion. The wells are washed with PBS and incubated at room temperature for one hour with blocking buffer (5% BSA in PBS). After washing with PBS, the primary antibody, 7SK (clone name: Alper-pCBP-1) is added in dilution buffer (45 µg/ml) (PBS buffer, 1% BSA, 0.01% Tween-20). The wells are washed with PBS/ 0.03% Tween-20 and incubated at room temperature for one hour with 100 µl/well secondary antibody (HRP-Donkey anti-mouse IgG, Jackson ImmunoResearch, West Grove, Pa.) diluted 1:3000. After washing the wells, 100 µl Immunopure TMB substrate solution (Pierce, Rockford, Ill.) is added. Color reaction is stopped by the addition of 100 µl/well 1N $H_2SO_4$ and the analysis is performed with an ELISA Reader. The figures represent optical density (OD) values of plasma readings for PCBP-1 levels.
Figure 8:
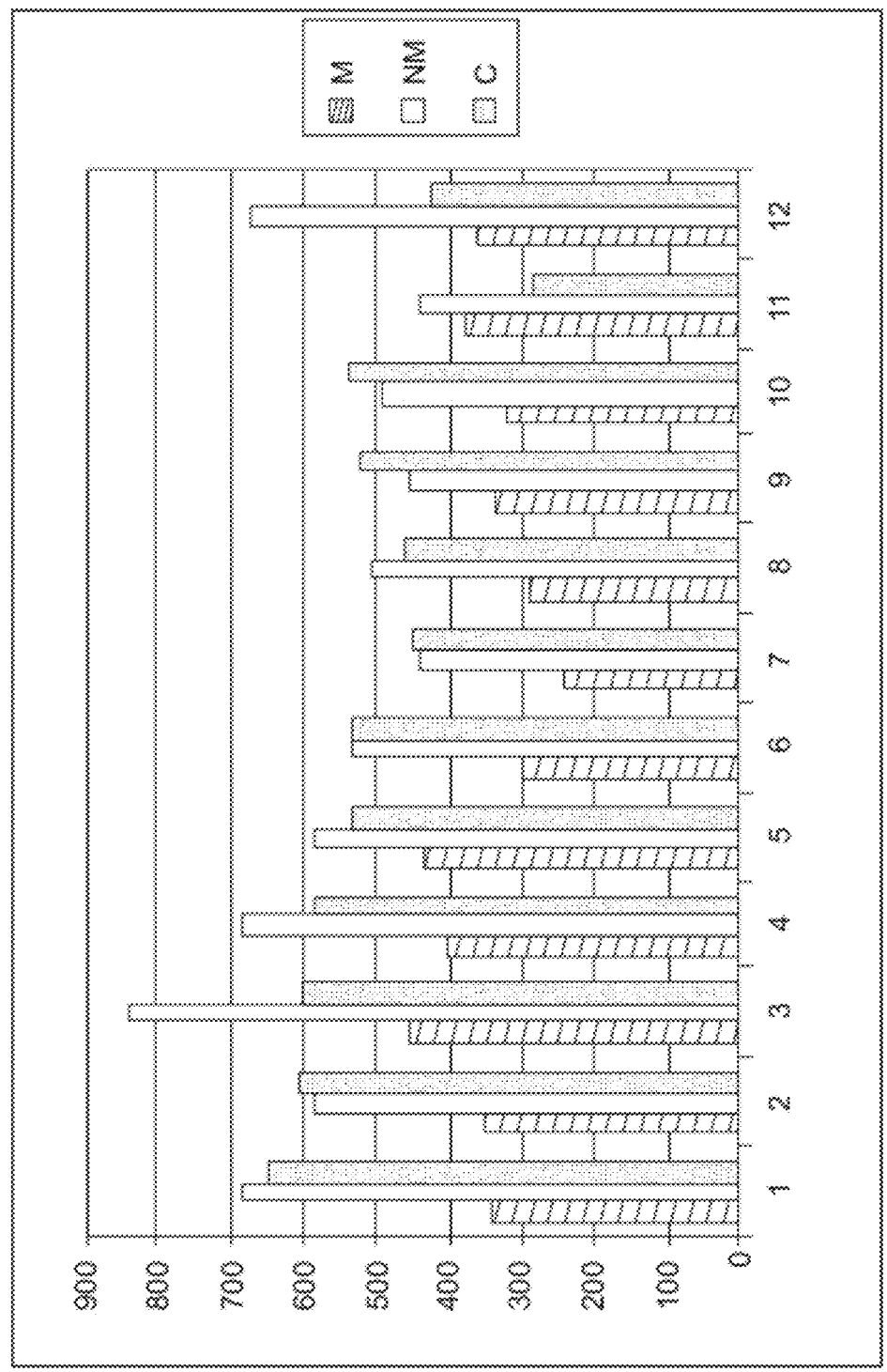
Figure 8:
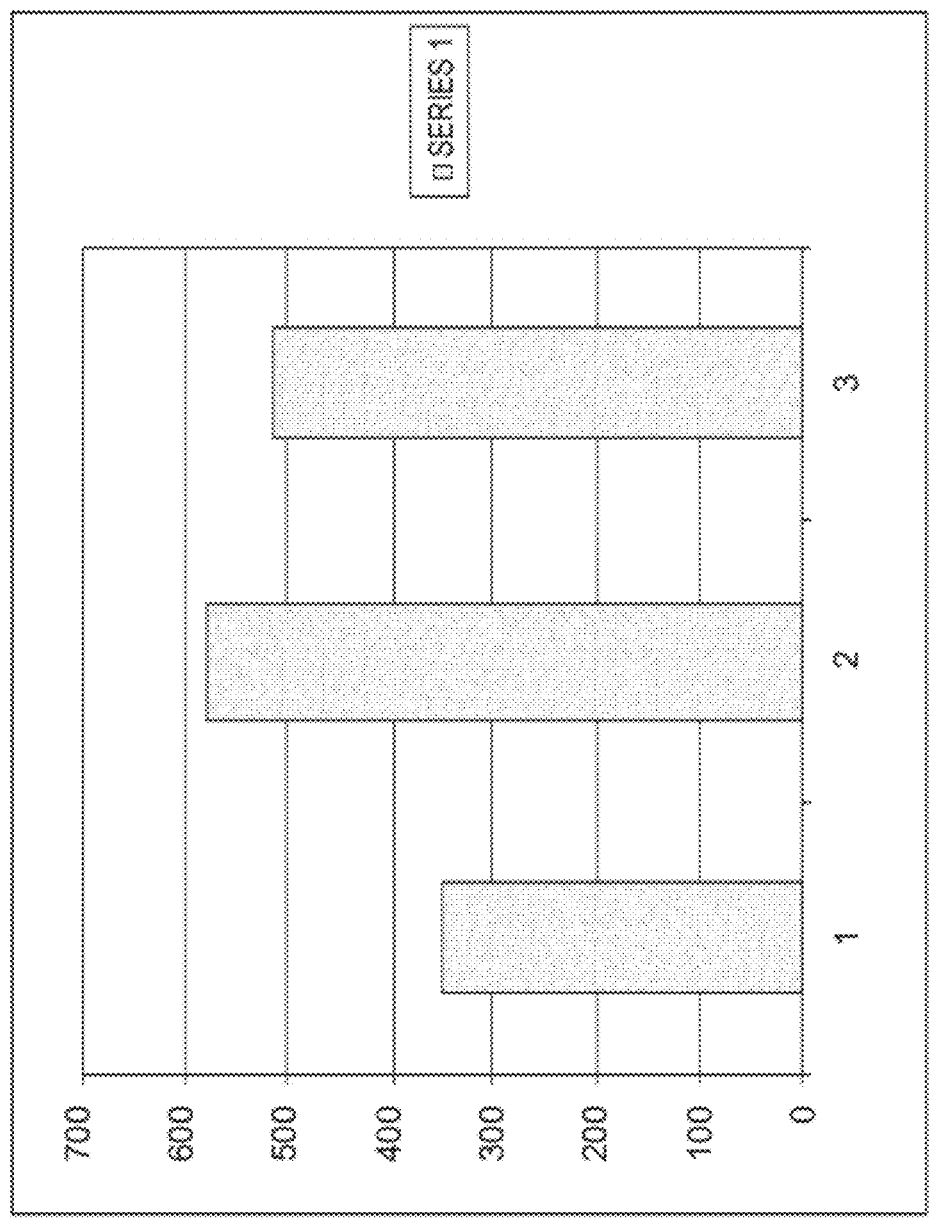

Plasma samples (C: control breast blood sample, NM: non-metastatic breast blood sample, M: metastatic breast blood sample) obtained from control and patient groups are diluted with PBS at a ratio of 1:100. Plasma PCBP-1 levels are measured with an enzyme-linked immunosorbent enzyme assay. The ELISA plates (Nalge NUNC International, Rochester, N.Y.) are coated with 100 µl/well of diluted plasma and incubated at 4° C. overnight. The blood plasma samples are analyzed in a blinded fashion. The wells are washed with PBS and incubated at room temperature for one hour with blocking buffer (5% BSA in PBS). After washing with PBS, the primary antibody, 7SK (clone name: Alper-pCBP-1) is added in dilution buffer (45 µg/ml) (PBS buffer, 1% BSA, 0.01% Tween-20). The wells are washed with PBS/0.03% Tween-20 and incubated at room temperature for one hour with 100 µl/well secondary antibody (HRP-Donkey anti-mouse IgG, Jackson ImmunoResearch, West Grove, Pa.) diluted 1:3000. After washing the wells, 100 µl Immunopure TMB substrate solution (Pierce, Rockford, Ill.) is added. Color reaction is stopped by the addition of 100 µl/well 1N $H_2SO_4$ and the analysis is performed with an ELISA Reader. The figures represent optical density (OD) values of plasma readings for PCBP-1 levels. See FIG. 8.

EXAMPLE 9

Figure 9:
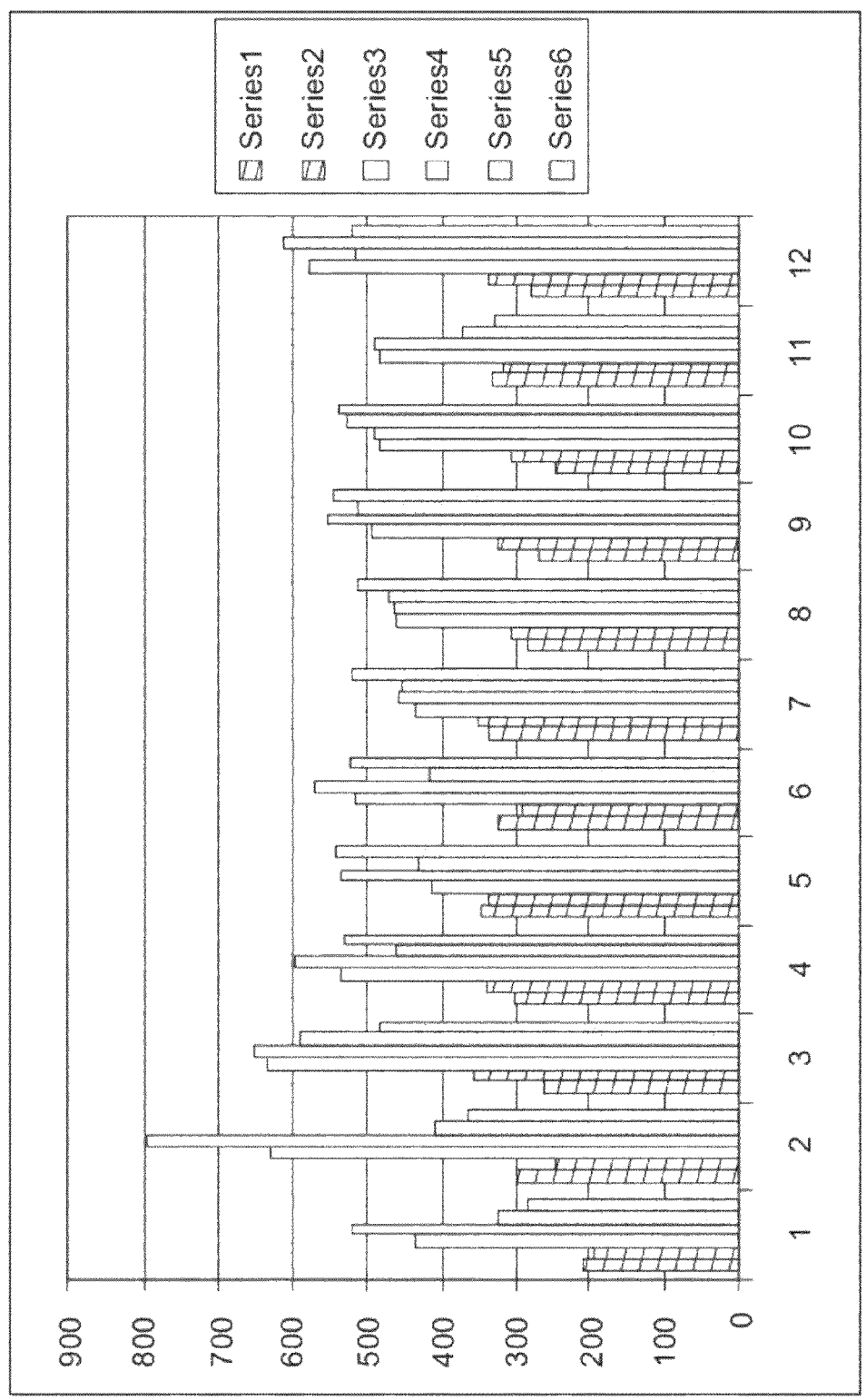
FIG. 9. Plasma samples (C: control breast blood sample, NM: non-metastatic breast blood sample, M: metastatic breast blood sample) obtained from control and patient groups are diluted with PBS at a ratio of 1:100. Plasma PCBP-1 levels are measured with an enzyme-linked immunosorbent enzyme assay. The ELISA plates (Nalge NUNC International, Rochester, N.Y.) are coated with 100 µl/well of diluted plasma and incubated at 4° C. overnight. The plasma samples are analyzed in a blinded fashion. The wells are washed with PBS and incubated at room temperature for one hour with blocking buffer (5% BSA in PBS). After washing with PBS, the primary antibody, Alper PCBP-1 mouse mAB (7SK) (clone name: Alper-pCBP-1) is added in dilution buffer (45 µg/ml) (PBS buffer, 1% BSA, 0.01% Tween-20). The wells are washed with PBS/0.03% Tween-20 and incubated at room temperature for one hour with 100 µl/well secondary antibody (HRP-Donkey anti-mouse IgG, Jackson ImmunoResearch, West Grove, Pa.) diluted 1:3000. After washing the wells, 100 µl Immunopure TMB substrate solution (Pierce, Rockford, Ill.) is added. Color reaction is stopped by the addition of 100 µl/well 1N $H_2SO_4$ and the analysis is performed with an ELISA Reader. Optical density is represented by OD and shows PCBP-1 levels in plasma. Series 1-2 represent controls, series 3-4 represent nonmetastatic and series 5-6 represent metastatic plasma samples. 1: metastatic, 2: nonmetastatic, 3: control plasma samples.

Plasma samples (C: control breast blood sample, NM: non-metastatic breast blood sample, M: metastatic breast blood sample) obtained from control and patient groups are diluted with PBS at a ratio of 1:100. Plasma PCBP-1 levels are measured with an enzyme-linked immunosorbent enzyme assay. The ELISA plates (Nalge NUNC International, Rochester, N.Y.) are coated with 100 µl/well of diluted plasma and incubated at 4° C. overnight. The plasma samples are analyzed in a blinded fashion. The wells are washed with PBS and incubated at room temperature for one hour with blocking buffer (5% BSA in PBS). After washing with PBS, the primary antibody, 7SK MoAb (clone name: Alper-pCBP-1) is added in dilution buffer (45 µg/ml) (PBS buffer, 1% BSA, 0.01% Tween-20). The wells are washed with PBS/0.03% Tween-20 and incubated at room temperature for one hour with 100 µl/well secondary antibody (HRP-Donkey anti-mouse IgG, Jackson ImmunoResearch, West Grove, Pa.) diluted 1:3000. After washing the wells, 100 µl Immunopure TMB substrate solution (Pierce, Rockford, Ill.) is added. Color reaction is stopped by the addition of 100 µl/well 1N $H_2SO_4$ and the analysis is performed with an ELISA Reader. Optical density is represented by OD and shows PCBP-1 levels in plasma. Series 1-2 represent controls, series 3-4 represent nonmetastatic and series 5-6 represent metastatic plasma samples. 1: metastatic, 2: nonmetastatic, 3: control plasma samples. See FIG. 9.

EXAMPLE 10

FWRs and CDRs of the heavy chain of the PCBP-1 mAb 7SK, in which the polypeptide sequence provided in the top line corresponds to the sequence of the PCBP-1 mAb. Amino acid residues are numbered using the convention of Kabat et al. The bold residues set forth in underlined text indicate the specificity determining residues (SDRs). See FIG. 10.

EXAMPLE 11

FWRs and CDRs of the light chain of the PCBP-1 mAb 7SK, in which the polypeptide sequence provided in the top line corresponds to the sequence of the PCBP-1 mAb. Amino acid residues are numbered using the convention of Kabat et al. The bold residues set forth in underlined text indicate the specificity determining residues (SDRs). See FIG. 11.

Example 12

Cell lysates from SKBR3 cells are run on a 2D polyacrylamide gel and proteins are transferred to a nitrocellulose membrane. Membranes are probed with PCBP-1 mAb. Spot 1, corresponding to PCBP-1, is cut out of a corresponding Coomassie-Blue stained 2D gel and subjected to tryptic digest. Tryptic peptides are analyzed by MALDI-TOF to determine the sequences of the digested peptides. All peptides obtained from the digest have sequences that correspond to the sequence of PCBP-1. See FIG. 12.

EXAMPLE 13

Tissue arrays containing tissue samples of various normal and human cancer tissues are subjected to immunohistochemistry using Alper PCBP-1 mouse monoclonal antibody (7SK). Slides of the 117-2 multi-tissue array, the YTMAF96 array and the YTMAF179-3 are deparrafinized and rehydrated with distilled water. Heat-induced epitope retrieval is performed at 95-101° C. in citrate buffer at pH 6.0 for 20 minutes, then the slides are allowed to cool to room temperature and are rinsed with Tris buffer. A peroxidase block is applied to the slides for 5 minutes, and the slides are again rinsed with Tris buffer. BACKGROUND SNIPER™ (Biocare Medical Products, Concord, Calif.) is applied to the slides for 5 minutes, and the slides are rinsed with Tris buffer. A 1:50 dilution of Alper PBCP-1 mouse monoclonal antibody is then applied to the array slides for 30 minutes at room temperature, followed by a Tris buffer rinse. MACH 3™ Probe (Biocare Medical Products, Concord, Calif., USA) is applied to the slides for 15 minutes, the slides are rinsed with Tris buffer, and MACH 3™ Polymer (Biocare Medical Products, Concord, Calif., USA) is then added to the slides for 15 minutes. After a rinse with Tris buffer, diaminobenzenetetrahydrochloride is applied to the slides for 5 minutes. The slides are then contacted with hematoxylin counterstain. Tissue arrays are analyzed via microscopy for staining intensity. Results are summarized in FIG. 13. Intensity of PCBP-1 staining is increased in colon cancer, melanoma, squamous carcinoma, glioblastoma, endometrial cancer, sarcoma and bladder cancers as compared to normal controls, while PCBP-1 intensity is decreased in ovarian cancer as compared to normal controls.

Normal breast epithelial cells showed a 1- to 3-fold increase in nuclear staining intensity while breast cancer cells showed 3-fold cytoplasmic and sometimes 2- to 3-fold nuclear staining intensity for PCBP-1. Colon cancer tissue epithelial cells showed a 3-fold increase in cytoplasmic PCBP-1 staining intensity compared to normal colon tissue epithelial cells. A 3-fold increase in cytoplasmic staining intensity was observed in both melanoma and squamous carcinoma cells, while normal skin cells showed weak nuclear staining for PCBP-1. A 2-fold increase in cytoplasmic staining was observed in Glioblastoma multiforme and astrocytomas, while no staining was observed in normal brain neurons and astrocytes. Sarcomas and bladder cancer cells showed 2- to 3-fold increases in cytoplasmic staining compared to normal muscle and normal bladder cells. While normal endometrial cells showed negative or weak cytoplasmic staining for PCBP-1, endometrial cancer cells showed a 3-fold increase in nuclear and cytoplasmic staining for PCBP-1. Normal ovarian epithelial cells showed a 3-fold increase in cytoplasmic and nuclear staining for PCBP-1 as compared to ovarian cancer cells.

EXAMPLE 14

The soluble, native form of PCBP-1 is purified from SKBR3 human breast cancer cell conditioned media. An affinity approach is taken, in which Alper PCBP-1 mouse monoclonal antibody is cross-linked to sepharose (i.e. CNBr-activated sepharose or similar kit available from GE Healthcare Bio-Sciences Corp., Piscataway, N.J., USA, or from Pierce Chemical Co., Rockford, Ill., USA) to purify the native PCBP-1 antigen. Conditioned media is generated and affinity purification of PCBP-1 is performed.

The purified PCBP-1 is characterized with respect to size (SDS-PAGE), purity (SDS-PAGE, SEC-HPLC, Western blot), and aggregation (Western blot). The stability of the purified PCBP-1 preparation is monitored over time by SDS-PAGE and SEC-HPLC. The purification can be scaled up using non-affinity techniques which can include, but are not limited to ion exchange chromatography, filtration, aqueous phase partitioning and/or counter-current chromatography.

EXAMPLE 15

Purified PCBP-1 is injected to six-week-old Balb/c mice and six-1b. NZW rabbits via iv, ip, or intramuscular routes using Kohler and Milstein's original injection and monoclonal antibody production conventional technique over a period of 3-5 months (Kohler et al., Nature 256(5517): 495-497, 1975). During the injections, at certain time intervals several test bleedings are performed to test immunologic response as well as antibody production in mice and rabbits. Production of monoclonal and polyclonal antibodies is tested using ELISA, western blot and immunofluorescence staining techniques.

What is claimed is:

1. A pharmaceutical composition comprising an antibody or antibody fragment specific for a PCBP-1 antigen, comprising a heavy chain variable domain comprising three complemenarity determining regions (CDRs) comprising the amino acid sequences of SEQ ID NO: 45, SEQ ID NO: 46 and SEQ ID NO: 47, and a light chain variable domain comprising three CDRs comprising the amino acid sequences of SEQ ID NO: 48, SEQ ID NO: 49 and SEQ ID NO: 50 and a pharmaceutically acceptable carrier.

2. The pharmaceutical composition according to claim 1 wherein said PCBP-1 antigen is a soluble protein having a molecular weight of about 40 kilodaltons as measured by gradient polyacrylamide gel electrophoresis.

3. The pharmaceutical composition of claim 1, wherein the antibody or antibody fragment is detectably labeled.

4. The pharmaceutical composition of claim 1 conjugated to a cytotoxic radionuclide, a cytotoxic drug, a cytotoxic protein, cytokine, radionuclide, drug, immunomodulator, therapeutic enzyme, or anti-proliferative agent.

5. The pharmaceutical composition of claim 1 capable of preferentially binding to a soluble or secreted form of PCBP-1 antigen, relative to a membrane form of PCBP-1.

6. An isolated DNA sequence which encodes the antibody or the antibody fragment of claim 1.

7. A vector comprising the DNA sequence of claim 6.

8. A host cell transformed with the vector of claim 7.

9. A process for the production of an antibody that binds to PCBP-1, comprising culturing the host cell of claim 8 and isolating the antibody.

10. A kit for the immunohistochemical detection of carcinoma comprising: (a) a monoclonal antibody specific for a PCBP-1 antigen comprising a heavy chain variable domain comprising three complemenarity determining regions (CDRs) comprising the amino acid sequences of SEQ ID NO: 45, SEQ ID NO: 46, and SEQ ID NO: 47, and a light chain variable domain comprising three CDRs comprising the amino acid sequences of SEQ ID NO: 48, SEQ ID NO: 49, and SEQ ID NO: 50 and (b) a secondary antibody conjugated to a detectable label.

11. The pharmaceutical composition of claim 1, capable of binding to a soluble form of PCBP-1 with a specific affinity of between $10^{-8}$ M and $10^{-11}$ M.

12. The pharmaceutical composition of claim 1, capable of selectively reducing the activity of a soluble PCBP-1 in a cell.

13. The pharmaceutical composition of claim 1, capable of recognizing an epitope selected from the group consisting of SEQ ID NOs: 1-14, and fragments thereof.

14. The pharmaceutical composition of claim 1 wherein the antibody or antibody fragment is humanized.

15. The pharmaceutical composition of claim 1, wherein the antibody or antibody fragment is conjugated to another protein or protein fragment to form a fusion protein.

* * * * *